United States Patent
Kloepfer et al.

(10) Patent No.: US 7,846,110 B2
(45) Date of Patent: Dec. 7, 2010

(54) SELF-CONTAINED TEST UNIT FOR TESTING BODY FLUIDS

(75) Inventors: Hans G. Kloepfer, Noblesville, IN (US); Thomas Kloepfer, Noblesville, IN (US); Reinhard Hafellner, Spielberg (AT)

(73) Assignee: Advanced Medical Products GmbH (AT)

( * ) Notice: Subject to any disclaimer, the term of this patent is extended or adjusted under 35 U.S.C. 154(b) by 0 days.

(21) Appl. No.: 11/832,475

(22) Filed: Aug. 1, 2007

(65) Prior Publication Data

US 2008/0033319 A1 Feb. 7, 2008

Related U.S. Application Data

(60) Provisional application No. 60/835,325, filed on Aug. 3, 2006.

(51) Int. Cl.
- A61B 5/00 (2006.01)
- A61B 17/14 (2006.01)
- A61B 17/32 (2006.01)
- A61B 17/34 (2006.01)
- B65D 81/00 (2006.01)

(52) U.S. Cl. ................ 600/584; 600/573; 600/583; 606/181; 606/182; 606/184; 606/185

(58) Field of Classification Search ............ 600/573, 600/583–584; 606/181, 182, 184, 185
See application file for complete search history.

(56) References Cited

U.S. PATENT DOCUMENTS

| | | | | |
|---|---|---|---|---|
| 3,760,809 A | * | 9/1973 | Campbell, Jr. | 606/182 |
| 4,230,118 A | * | 10/1980 | Holman et al. | 606/182 |
| 4,414,975 A | * | 11/1983 | Ryder et al. | 606/182 |
| 4,539,988 A | * | 9/1985 | Shirley et al. | 606/182 |

(Continued)

FOREIGN PATENT DOCUMENTS

EP 1202057 A3 5/2002

(Continued)

OTHER PUBLICATIONS

Feb. 12, 2009, PCT International Search Report, Advanced Medical Products GMBH et al.., International Application No. PCT/US2007/017211.

*Primary Examiner*—Max Hindenburg
*Assistant Examiner*—Sean P Dougherty
(74) *Attorney, Agent, or Firm*—E. Victor Indiano; Indiano Law Group

(57) ABSTRACT

A self contained disposable test unit for testing body fluid comprises a body member and a support member. The support member is moveable with respect to the body member between a first position and a second position. The support member includes a body part receiving surface for receiving a patient's body part. A lancet is carried by the body member and includes a lancet tip capable of piercing the skin of a patient to produce fluid flow. A test member is capable of interacting with body fluid to aid in the determination of information about body fluid components. A capillary member is capable of directing fluid flow to the test member. A pressure cup is capable of exerting pressure on a body part to foster fluid flow out of a lanced site and into the capillary, and a calibration member is provided for containing information for facilitating calibration of the test unit.

41 Claims, 22 Drawing Sheets

U.S. PATENT DOCUMENTS

| | | | | |
|---|---|---|---|---|
| 4,628,929 | A * | 12/1986 | Intengan et al. | 606/182 |
| 4,643,189 | A * | 2/1987 | Mintz | 606/182 |
| 4,715,374 | A * | 12/1987 | Maggio | 606/182 |
| 4,844,095 | A * | 7/1989 | Chiodo et al. | 606/182 |
| 4,983,178 | A * | 1/1991 | Schnell | 606/181 |
| 5,212,879 | A * | 5/1993 | Biro et al. | 29/437 |
| 5,314,441 | A * | 5/1994 | Cusack et al. | 606/182 |
| 5,630,828 | A * | 5/1997 | Mawhirt et al. | 606/187 |
| 5,645,555 | A * | 7/1997 | Davis et al. | 606/182 |
| 5,797,940 | A * | 8/1998 | Mawhirt et al. | 606/167 |
| 5,851,215 | A * | 12/1998 | Mawhirt et al. | 606/181 |
| 5,891,053 | A * | 4/1999 | Sesekura | 600/583 |
| 5,951,492 | A * | 9/1999 | Douglas et al. | 600/583 |
| 5,951,582 | A * | 9/1999 | Thorne et al. | 606/182 |
| 5,962,215 | A * | 10/1999 | Douglas et al. | 435/4 |
| 6,042,595 | A * | 3/2000 | Morita | 606/181 |
| 6,132,449 | A | 10/2000 | Lum et al. | |
| 6,221,089 | B1 * | 4/2001 | Mawhirt | 606/181 |
| 6,358,265 | B1 * | 3/2002 | Thorne et al. | 606/181 |
| 6,364,890 | B1 | 4/2002 | Lum et al. | |
| 6,535,112 | B1 * | 3/2003 | Rothschink | 340/425.5 |
| 6,696,240 | B1 | 2/2004 | Kloepfer et al. | |
| 6,783,502 | B2 * | 8/2004 | Orloff et al. | 600/583 |
| 6,808,499 | B1 * | 10/2004 | Churchill et al. | 600/587 |
| 6,840,912 | B2 | 1/2005 | Kloepfer et al. | |
| 6,849,052 | B2 * | 2/2005 | Uchigaki et al. | 600/584 |
| 7,052,652 | B2 | 5/2006 | Zanzucchi et al. | |
| 7,150,755 | B2 * | 12/2006 | Levaughn et al. | 606/181 |
| 7,235,056 | B2 * | 6/2007 | Duchon et al. | 600/583 |
| 7,299,081 | B2 * | 11/2007 | Mace et al. | 600/345 |
| 7,374,545 | B2 * | 5/2008 | Alroy | 600/583 |
| 7,374,959 | B2 | 5/2008 | Koh | |
| 7,427,377 | B2 | 9/2008 | Zanzucchi et al. | |
| 7,452,365 | B2 * | 11/2008 | Galloway et al. | 606/167 |
| 2002/0177761 | A1 * | 11/2002 | Orloff et al. | 600/309 |
| 2002/0177788 | A1 * | 11/2002 | Hodges et al. | 600/583 |
| 2003/0093010 | A1 * | 5/2003 | Essenpreis | 600/583 |
| 2003/0109777 | A1 * | 6/2003 | Kloepfer et al. | 600/367 |
| 2004/0028558 | A1 | 2/2004 | Pollock et al. | |
| 2004/0138588 | A1 * | 7/2004 | Saikley et al. | 600/583 |
| 2004/0225312 | A1 * | 11/2004 | Orloff et al. | 606/182 |
| 2004/0236251 | A1 * | 11/2004 | Roe et al. | 600/583 |
| 2004/0267229 | A1 * | 12/2004 | Moerman et al. | 604/500 |
| 2004/0267300 | A1 * | 12/2004 | Mace | 606/182 |
| 2005/0033196 | A1 * | 2/2005 | Alroy | 600/573 |
| 2005/0033341 | A1 * | 2/2005 | Vreeke et al. | 606/181 |
| 2005/0065414 | A1 | 3/2005 | Allen et al. | |
| 2005/0096565 | A1 * | 5/2005 | Chang | 600/584 |
| 2005/0154410 | A1 * | 7/2005 | Conway et al. | 606/181 |
| 2005/0228313 | A1 * | 10/2005 | Kaler et al. | 600/583 |
| 2006/0034728 | A1 | 2/2006 | Kloepfer et al. | |
| 2006/0072004 | A1 | 4/2006 | Fujita | |
| 2006/0100543 | A1 * | 5/2006 | Raney et al. | 600/583 |
| 2006/0222567 | A1 | 10/2006 | Kloepfer et al. | |
| 2006/0229532 | A1 * | 10/2006 | Wong et al. | 600/583 |
| 2006/0264778 | A1 * | 11/2006 | Lim et al. | 600/576 |
| 2006/0264997 | A1 * | 11/2006 | Colonna et al. | 606/181 |
| 2006/0292039 | A1 | 12/2006 | Iida | |
| 2007/0015198 | A1 | 1/2007 | Harvey | |
| 2007/0233166 | A1 * | 10/2007 | Stout | 606/182 |
| 2007/0233395 | A1 * | 10/2007 | Neel et al. | 702/19 |
| 2008/0009766 | A1 * | 1/2008 | Holmes et al. | 600/583 |
| 2008/0208077 | A1 * | 8/2008 | Iddan et al. | 600/582 |

FOREIGN PATENT DOCUMENTS

| | | |
|---|---|---|
| EP | 1625823 | 5/2006 |
| WO | WO 03/049609 | 6/2003 |

* cited by examiner

SELF-CONTAINED TEST UNIT FOR TESTING BODY FLUIDS

PRIORITY CLAIM

The present application claims the benefit of Hafellner, Kloepfer and Kloepfer, U.S. Provisional Patent Application No. 60/835,325 that was filed on 3 Aug. 2006. The entirety of this provisional application is specifically incorporated into this application.

I. TECHNICAL FIELD OF INVENTION

The present invention relates to testing devices used for obtaining a sample of body fluids, and then testing that body fluid, normally in conjunction with a testing device such as a meter.

II. BACKGROUND OF THE INVENTION

In the maintenance of health, it is often desirable to test body fluids for the presence or absence of particular substances. To this end, many testing devices have been invented previously by the Applicants and others. Testing devices invented by the applicant are shown in Kloepfer et al., U.S. Pat. Nos. 6,696,240; 6,840,912; and Published Application Nos. EP 01309073.3 (published as EP 1202057A3 on 2 May 2002); EP 02794170.7 (published as EP 1450675A1 on 19 Jun. 2003); U.S. Ser. No. 10/916,292 (published as US 2006/0034728 on 16 Feb. 2006); and EP 05107323.7 (published as EP 1625823A3 on 3 May 2003)

Currently, a need exists for a test unit that is self-contained insofar as it comprises a unitary unit that contains all of the primary "disposable" components required for typical body fluid testing. These disposable components include a lancet for piercing the skin, and a testing area, wherein the fluid (usually blood) that is sought to be obtained, and that flows from the lanced skin after the skin has been lanced, can be separated and is separated into a plasma component and a fraction containing other components. On such a testing device, the plasma reacts with the reagents on the test member to form reagent-bound (or reagent-reacted) reactant compounds that can be used to quantitatively or semi-quantitatively determine the presence or absence of a substance within the blood such as glucose or cholesterol.

To this end, the readers attention is directed particularly to Kloepfer et al., U.S. Pat. No. 6,840,912 (the "Test Wand" Patent), that discloses a self-contained test wand. The self-contained test wand shown in the Kloepfer patent includes a unitary device that includes the following four components: (1) a spring-loaded lancet capable of piercing the skin; (2) a pressure cuff that contains an annular lip for exerting pressure around the lancing site, that helps foster the flow of blood out of the lanced site; (3) a swab that is provided for cleaning the lanced site before and after the lancing of the site; and (4) a test member that includes means for separating the cellular components of blood from the plasma components.

The test member also includes one or more reagents that can react with the components of interest in the plasma of interest, to thereby convert these components into reagent reactive components that can then be employed to determine the quantity of the components of interest. The test wand is designed to be used in connection with a meter, such as the one glucose meter disclosed in Kloepfer et al., U.S. Published Patent Application No. 2006-0034728 (16 Feb. 2006) (the "Meter Patent"). The meter disclosed in the above-referenced Kloepfer patent application employs either reflectance or transmittance photometry techniques to determine the quantity of the component of interest.

The reader's attention is directed to the above-referenced Kloepfer patents and patent applications, both for their disclosure of various devices, and for their discussion of the need for testing such body components, the chemical aspects of testing for such components, and the disease and social aspects of the reasons for the testing for such components.

Although the test wand(s) disclosed in the various Kloepfer patents perform their intended function in a most admirable manner, room for improvement still exists. In particular, room for improvement exists in producing alternative test wand units that may be smaller, and thereby take up less room; or that may be less expensive to produce, or, that may be better adapted to use in connection with other types of meters, such as the meter disclosed in Applicants'co-pending mobile transmission device meter patent application, U.S. Published Patent Application No. 2006-0222,567 (5 Oct. 2006) (the "Cell Phone" Patent). Another desire is to provide a device that has improved performance, when compared to devices shown in the earlier Kloepfer references.

III. SUMMARY OF THE INVENTION

In accordance with the present invention, a self contained disposable test unit for testing body fluid comprises a body member and a support member. The support member is moveable with respect to the body member between a first position and a second position. The support member includes a body part receiving surface for receiving a patient's body part. A lancet is carried by the body member and includes a lancet tip capable of piercing the skin of a patient to produce fluid flow. A test member is capable of interacting with body fluid to aid in the determination of information about body fluid components. A capillary member is capable of directing fluid flow to the test member. A pressure cup is capable of exerting pressure on a body part to foster fluid flow out of a lanced site and into the capillary, and a calibration member is provided for containing information for facilitating calibration of the test unit.

Preferably, the lancet is moveable between a storage position, a piercing position and a retracted position. In the storage position, the lancet tip is disposed below the body part receiving surface of the support member. In the piercing position, the tip is disposed above the body part receiving surface of the support member. In the retracted position, the tip is disposed below the body part receiving surface of the support member. The lancet is moved into the retracted position through the engagement of the support member with the lancet as the support member moves between the first and second position.

Preferably, the piercing position of the lancet is adjustable to permit the user to vary a distance into which the lancet can penetrate the skin when in the piercing position. Additionally, when the lancet is in the storage position, the lancet is preferably carried by the body portion in a fixed position. The support member preferably includes at least a first and a second surface that are selectively engageable with the lancet for moving the lancet into the retracted position. The first and second selectively engageable surfaces are axially offset, such that when the first surface engages a lancet, the depth to which the tip will penetrate the skin is different than the depths to which the tip will penetrate the skin when the second surface engages the lancet.

One feature of the present invention is that the support member and the body member are moveable with respect to each other. This feature has the advantage of enabling the device to function with fewer parts than many prior known devices.

The movement of the body member and support member relative to each other permits the lancet to move from a storage position, where it cannot stick the user, to a piercing position, wherein the lancet can pierce the user to cause a fluid flow. Continued movement of the support member relative to the body member causes the lancet to then move into a retracted position, where it no longer is capable of piercing the user. In most cases, the user's skin is being pierced, and the fluid that is caused to flow from the lanced site is blood.

The combination of these features enables the device to provide a mechanism for sticking the user with lancet in a quick and relatively painless manner that pierces the skin, while quickly removing the lancet, so that it does not remain imbedded within the user.

Another feature of the present invention is that it includes a lancet position adjustor for permitting the user to vary the distance into which the lancet can penetrate the skin when in a piercing position.

This feature has the advantage of enabling the device to be better suited to different users, by enabling the user to vary the piercing depth of the lancet. This enables the user to better select a minimum piercing depth that will both pierce the skin sufficiently so as to cause a sufficient flow of blood, without being inserted any deeper than necessary, and thereby cause any more pain, or greater flow of blood than is necessary.

These and other features of the present invention will become apparent to those skilled in the art upon a review of the drawings and detailed description presented below, that represent the best mode perceived presently of practicing the invention by the Applicants.

IV. BRIEF DESCRIPTION OF DRAWINGS

V. DETAILED DESCRIPTION OF THE PREFERRED EMBODIMENT

The testing device 10 of the present invention is best shown and described initially with reference to FIGS. 1-8.

Figure 29:
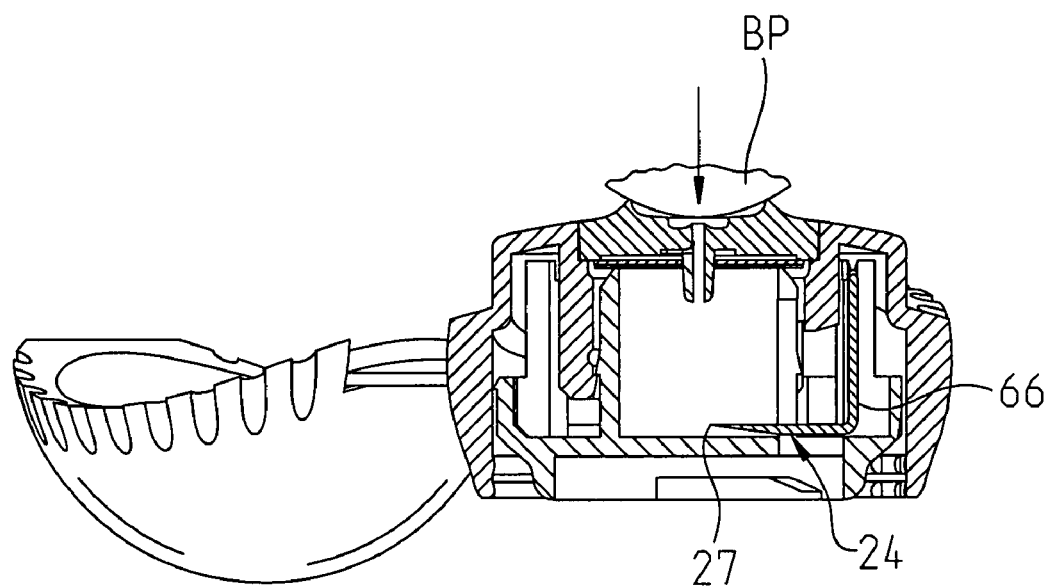
FIG. 29 is a sectional view showing the lancet in the fully retracted position and the body member and support member in their second, or fully compressed positions.

The primary components of the testing device 10 include a body member 14 and a support member 18. The support member 18 is moveable with respect to the body member 14 between a first position (FIG. 22) and a second position (FIG. 29). As will be discussed in more detail below, when the body member 14 and support member 18 are assembled, they share generally a common axis, such that when in the first or expanded position, the body member 14 and support member 18 are moved relatively away from each other, so that the height of the testing device 10 is relatively maximized. When in the second position, the body member 14 and support member 18 are moved axially toward each other so as to compress the testing device 10, so that the height of the testing device is at its relative shortest. The support member 18 includes a body part receiving surface 20, for receiving a patient's body part.

The testing device 10 also includes a lancet 24 that is carried by the body member 14, and is pivotably coupled to the body member 14 by the lancet 24 being coupled to a lancet support 26. The lancet includes a tip 27 that terminates in a point. A reagent containing test member 28 and calibration component 30 are also provided.

As best shown in FIGS. 22-29, prior to the testing device being used, the lancet is normally positioned in a storage position (FIG. 22) wherein the lancet tip 27 is disposed below the body part receiving surface 20 of the support member 18. The lancet 24 is moveable into a piercing position (FIG. 27) wherein the tip 27 is disposed above the body part receiving surface 20 of the support. The lancet 24 is also moveable into a retracted position (FIG. 29) wherein the tip is disposed below the body part receiving surface 20 of the support member 18. As will be described in more detail below, the lancet 24 is moved into the retracted position through the engagement of the support member 18 with the lancet 24 as the support member 18 moves between its first (or expanded) position and its second (or compressed) position. The "movement" of the lancet 24 from its storage to its piercing position actually occurs through the movement of the support member 18 relative to the generally stationary body member 14 and lancet 24.

Figure 2:
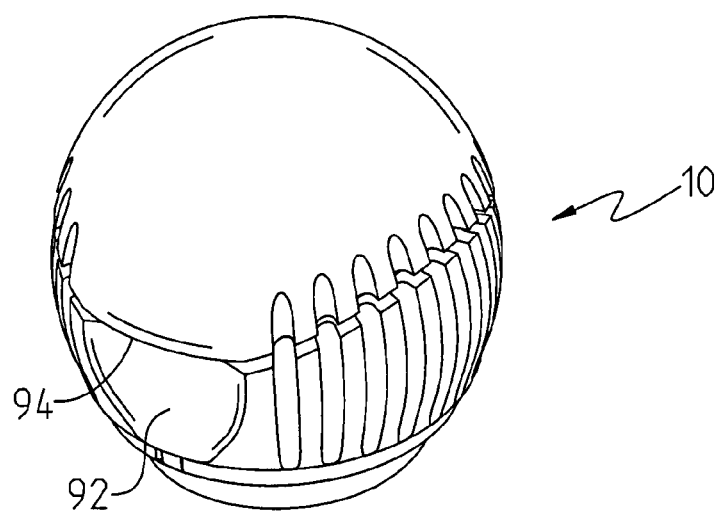
FIG. 2 is a perspective view, similar to FIG. 1, except rotated 90 degrees, showing the cap in its closed position.
Figure 6:
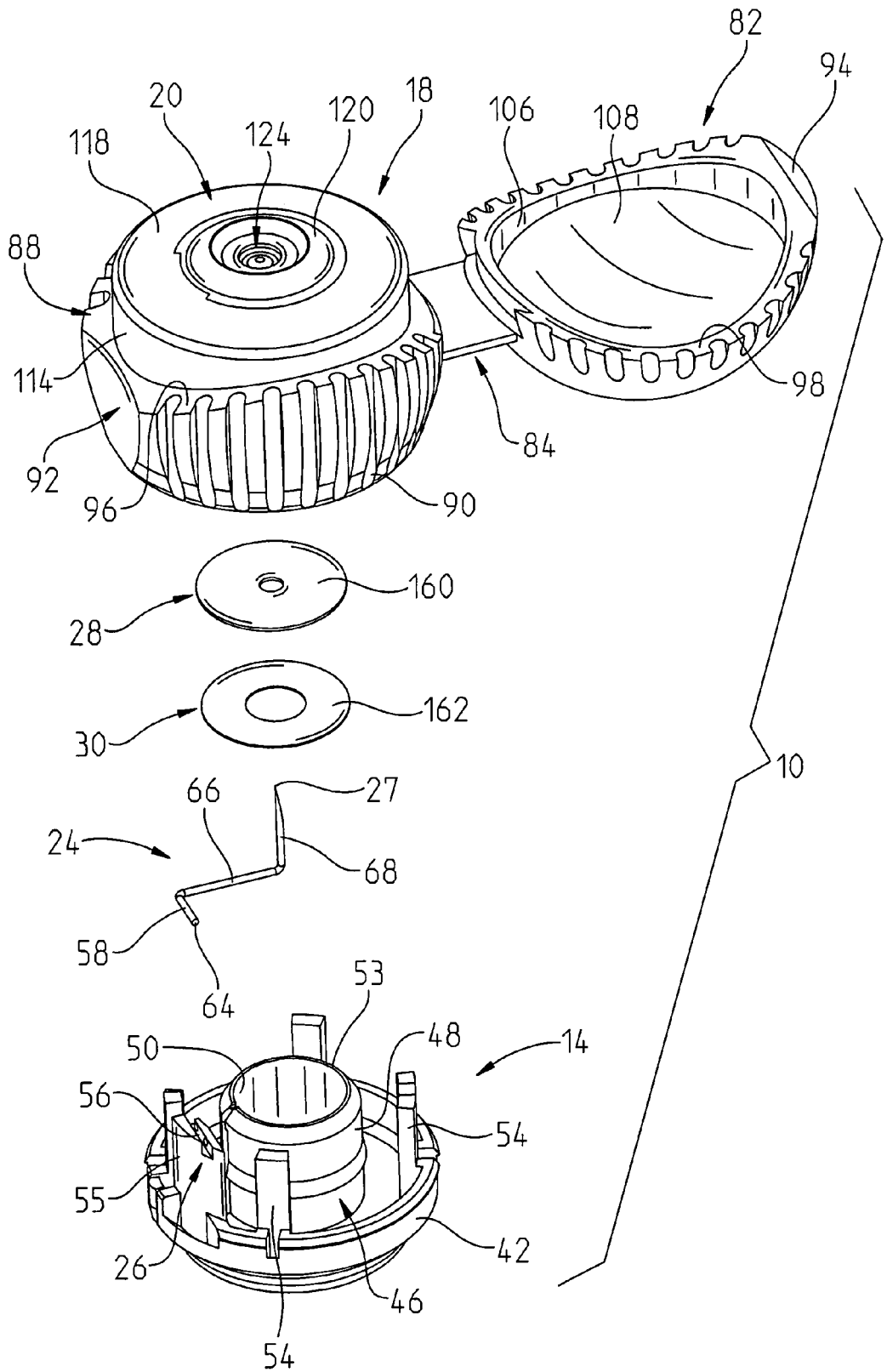
FIG. 6 is an exploded view of the present invention.
Figure 7:
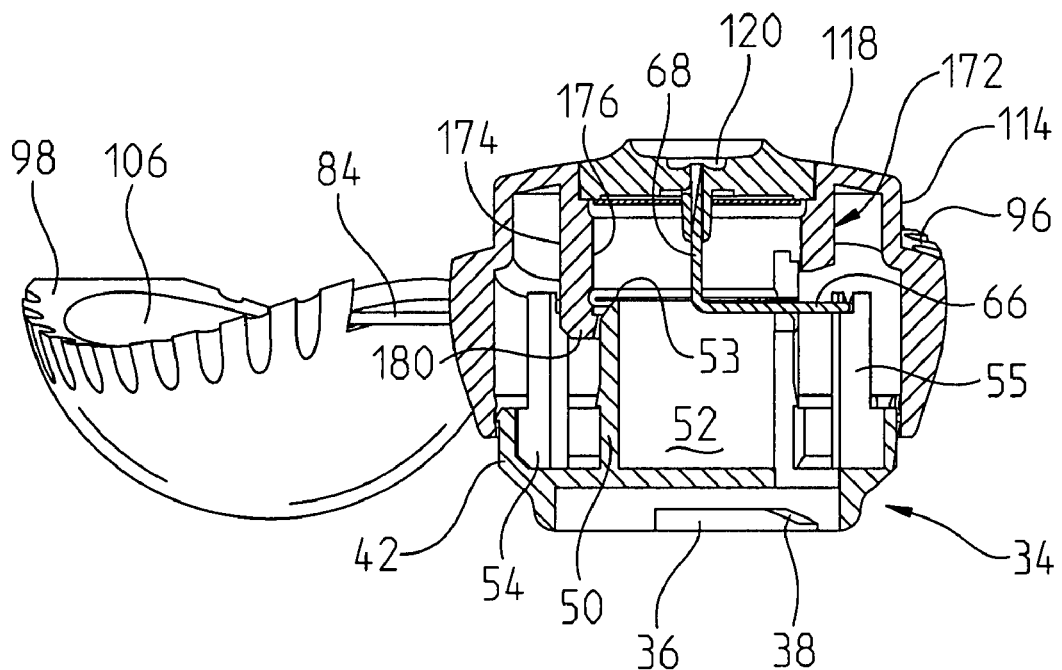
FIG. 7 is a sectional view taken along lines 7-7 of FIG. 1.

The body member 14 can best be understood with reference to FIG. 2, 6 and 7. The body member 14 includes a base portion 34 that also serves as a coupler, for coupling the testing device 10 to a meter such as the cell phone type meter 35 shown in FIG. 18. The base 34 should have a generally planar lip, so that the base can be supported on a surface, such as a counter top.

An aperture 34 is formed on the underside of the base 34, and is defined by an annular ring like member 38, that also comprises a bayonet-type coupling, to permit the testing device to be coupled to the cell phone like meter 35. A bayonet-type mounting provides a quick coupling and release mechanism for coupling and uncoupling the testing device 10 to the cell phone meter 35.

The body member 14 also includes a cylindrical perimetral base wall 42 that extends above, and has a slightly larger diameter than the base 34. The body member also includes a cylindrical, axially extending tube 46 that is disposed centrally on the body member 14. The cylindrical tube 46 has an axially extending, radially outwardly facing exterior wall 48, and an axially extending, radially inwardly facing interior wall 50. Interior wall 50 defines a hollow interior 52 that extends generally between aperture 38, and the upper edge 53 of the cylindrical tube 46.

The body member 14 also includes four, equi-distantly spaced support guide members 54 that are separated from each other at approximately 90 degrees. The upstanding support guide members 54, extend axially, generally parallel to the axis of the body member 14 and are provided for receiving an interior surface of the support member, to appropriately position the support member 18 on the body member 14, so that the support member 18 can move between its first or expanded position and its compressed position. The body member also includes a lancet support member 55. Lancet support 55 includes an angled upper surface that includes a groove 56. Groove 56 is sized and positioned for receiving the proximal leg 58 of the lancet 24. Preferably, groove 56 is sized and positioned so that the proximal leg 58 can be snap-fit into groove 56, so that leg 58 will be pivotably moveable within groove 56, but still will be retained within groove 56.

The lancet 24 (FIG. 6) includes a first end 64 that is disposed adjacent to the proximal leg 58, and an intermediate, radially extending portion 66. The radially extending portion 66 is so named because, when the lancet 24 is in its storage position, the portion 66 will extend in a general radial direction. However, it will be appreciated that the name given this component, as with the name given to the distal or axial portion 68 of the lancet, should not be confined to specific directions, and that the claims should always be construed broadly enough to include devices wherein the various legs, such as legs 58, 66 and 68 are disposed in other directions.

As alluded to above, the distal leg 68 is also referred to herein as an axially extending leg or portion, because when the lancet 24 is in its rest or storage position, the portion 68 will generally extend axially, so that it can fit through the aperture 130 within the body part supporting surface. It should also be noted that when in the retracted position (of FIG. 15), the radially extending portion 66 of the lancet will actually extend in an axial direction, and the axially extending leg 68 will actually extend in a radial direction.

Figure 16:
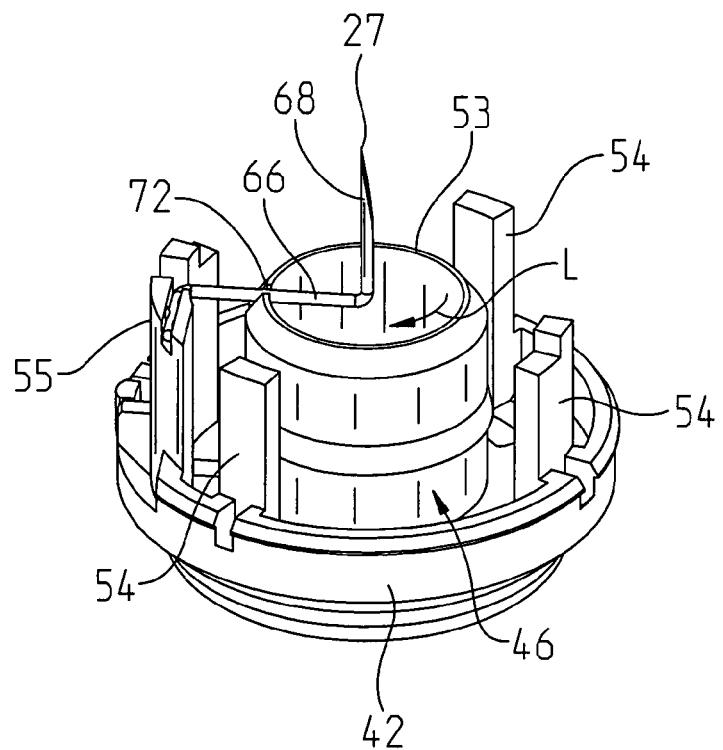
FIG. 16 is a perspective view of the body member showing a lancet in the storage and piercing position.
Figure 17:
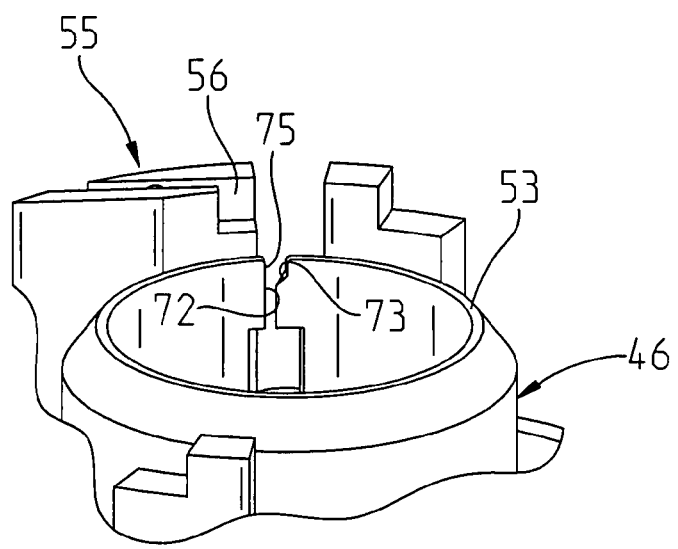
FIG. 17 is a perspective view of the body member, highlighting the lancet resisting surface.

Turning now to FIGS. 16 and 17, it will be noted that the cylindrical tube 46 does not comprise a totally endless cylinder. Rather, the cylinder 46 includes an axially extending slot 72. The slot includes an angled shelf 73. The angled shelf 73, along with axially extending wall 75 defines slot 72, which together cooperate to form a lancet movement resistant surface for resisting pivotal movement of the lancet 24.

As best shown in FIG. 16, the lancet 66, when in the storage position is positioned so that the radially extending leg 66 extends generally radially, and rests upon angled shelf 74. Pivotal movement of the lancet 24 in a direction indicated generally by arrow L in FIG. 16, causes the radially extending leg 66 to move through slot 72. The use of the angled shelf 73, and the spacing between the side walls 25 of the slot 72 permits the lancet to move through the slot 72, only by overcoming a predetermined amount of resistance, to thereby prevent the lancet 24 from free falling unimpededly through the slot 72.

This resistance in the movement of the lancet 24 that is induced by the slot 72 helps to ensure that the lancet 24 will penetrate the skin of the user, and that the position of the lancet 24 with the tip 27 pointed upwardly will not be so weakly held so as to be unable to penetrate the skin.

Figure 1:
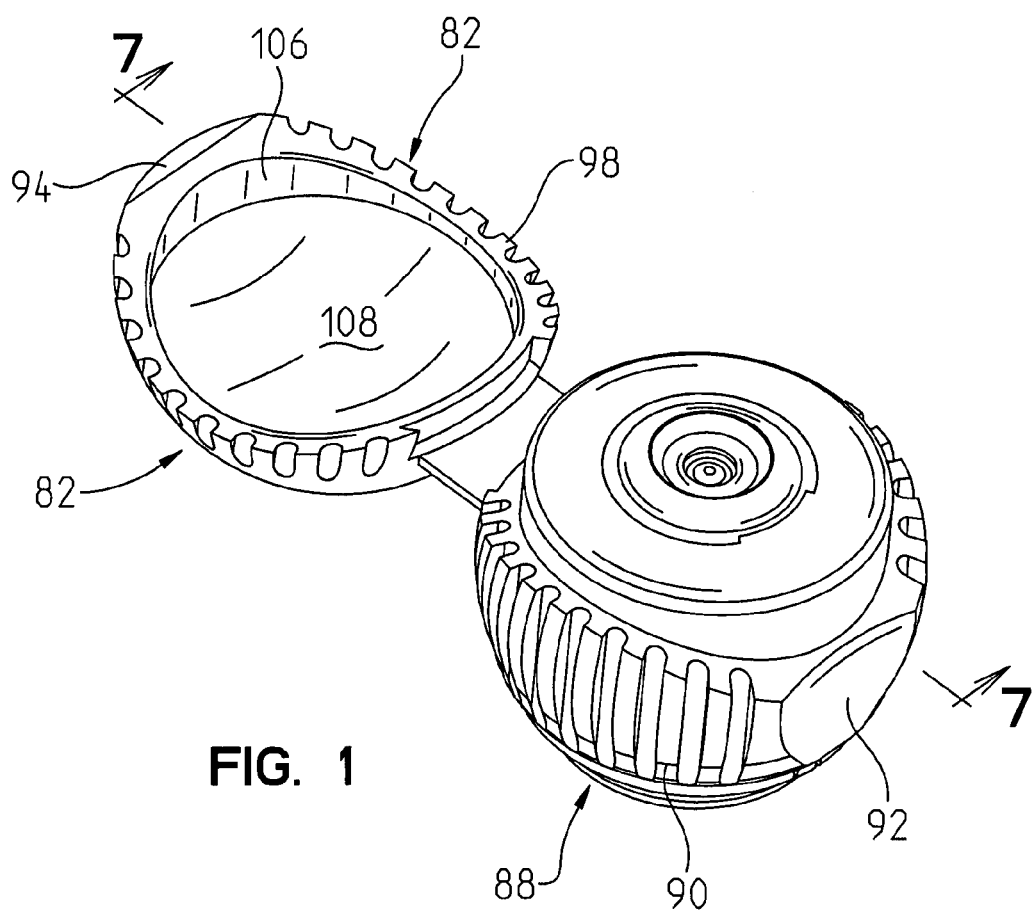
FIG. 1 is a perspective view of the present invention showing the cap member in its open position.
Figure 3:
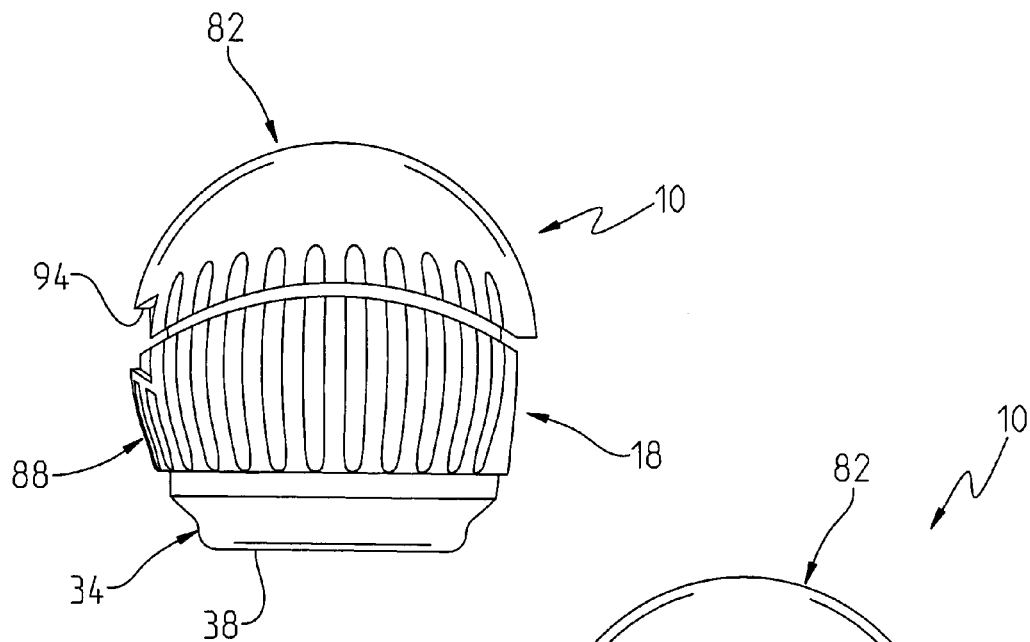
FIG. 3 is a rear elevational view of the present invention.
Figure 4:
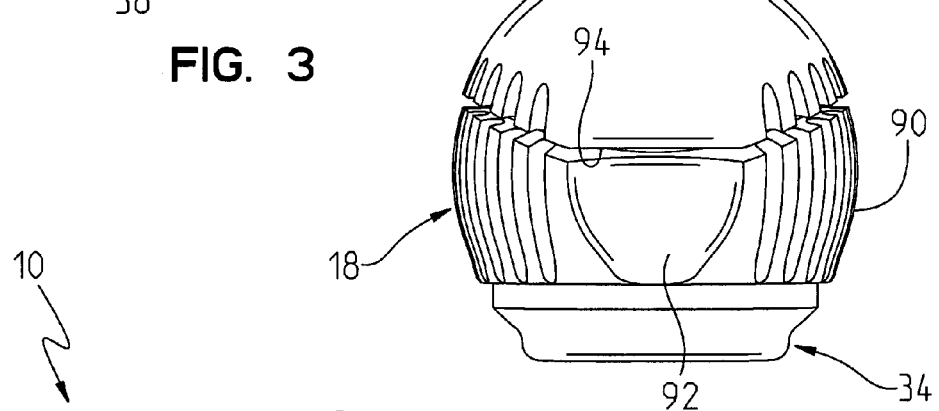
FIG. 4 is a front elevational view of the present invention.
Figure 5:
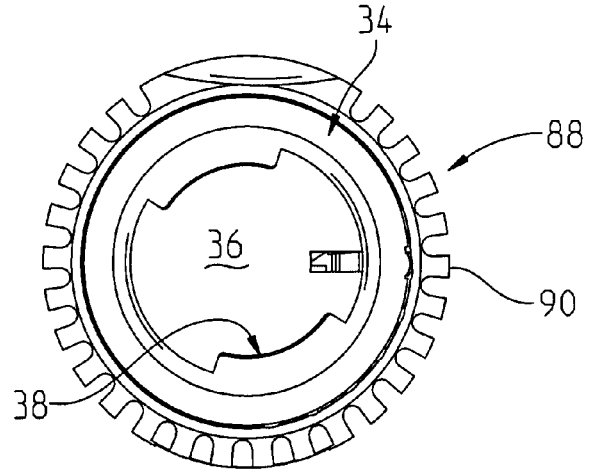
FIG. 5 is a bottom plan view of the present invention.

The support member 18 has a cap 82 attached to it by a strip of plastic that comprises a living hinge 84. The cap 82 is able to move about the living hinge 84 from an open position, such as shown in FIG. 1 where the body part receiving surface 20 is exposed, and is exteriorly disposed, and a closed position, such as shown in FIGS. 2-4. In the closed position, the cap 82 is disposed in a co-axial relationship with the support member 18, so that the body part receiving surface 20 is captured interiorly within the interior of the cap 82.

The support member 18 includes an axially extending, radially outwardly facing exterior wall 88, that includes a knurled or ribbed surface 90, for facilitating the user's ability to grasp the testing device 10. The outer surface 88 also includes a small concave portion 92, that, when the cap 82 is in its closed position, the concave portion 92 is disposed adjacent to the overhanging lip 94 of the cap. The overhanging lip 94 extends radially outwardly past the concave surface 92, so that the user can place his finger under the lip 94, to open the cap 82.

The upper edge of the knurled surface 90 terminates in an axially facing, radially extending circumferential mating surface 96, that is sized and positioned for mating with the axially facing, radially extending circumferential lip 98 of the cap 82.

The cap 82 also includes a frusto-spherical exterior surface 104 that terminates at its lower end, at the axially facing circumferential lip 98. As discussed above, the circumferential lip 98 also includes an overhanging lip portion 94, that is placeable in an opposed, and adjacent relation to the small concave surface 92 to form the opening handle. The cap 82 includes a frusto-spherical interior wall 106. Preferably, a cleansing pad 108, such as an alcohol soaked cleansing pad 108 is placed within the hollow interior defined by the interior wall 106. When the user is using the testing device 10, the cleansing pad 108 comes in handy, because the user should use the cleansing pad 108 to cleanse the skin adjacent of the body part that is to be lanced in order to draw blood from the user. Preferably, the lance site is cleansed before and after the site is lanced.

The support member 18, as best shown in FIGS. 1, 6, 7 and 9B includes a testing assembly 118, that includes the body part receiving surface 120, and a radially outwardly first facing, axially extending side surface 114. Axially extending side surface 114 and body part support surface 20 are normally designed to be disposed interiorly, within the interior of cap 82, when the device is in its closed position as is shown in FIG. 4. However, when the cap 82 is opened, the body part receiving surface 20 and axially extending surface 114 become exteriorly disposed. The body part receiving surface 120, includes several segments or parts, including a beveled, perimetral edge 117, and a radially outwardly disposed ring-like portion 118, that is disposed radially inwardly of the beveled perimetral edge.

An elevated, mound-like annular lip 120 is disposed radially interiorly of the radially outwardly disposed portion 118, and comprises an endless ring. As will be described in more detail below, the elevated annular lip 120 serves as a pressure cup, that is capable of exerting pressure against the skin of the user, when the user presses his finger against the elevated annular lip 120 so that the user's skin engages the surface of the elevated annular lip 120. When the annular lip 120 serves as a pressure cup, the pressure placed upon the user helps to foster the flow of body fluid, and in particular, blood out of a lanced site.

By using a pressure cup, such as that provided by the annular lip 120, several advantages are obtained. A first obtained advantage is that a smaller lanced "hole" in the user's skin can be used, because the pressure induced by the pressure cup can overcome the smallness of the hole, to still permit a sufficient amount of blood to flow out of the lanced hole, to enable the test to be performed properly. Additionally, the use of the pressure cup enables the user to use a non-traditional lancing site. In this regard, the finger tips are the most typical place for a user to lance his skin to obtain blood for a blood test. Finger tips are chosen because of the high rate of blood flow through the finger tips.

Other areas do not give up blood as easily, such as forearms and the like. However, the use of a forearm or other body part area has an advantage over the fingers, because it is not as densely populated with nerves, and as such, lancing in a site such as the forearm will generally not hurt as much. Additionally, the forearm is not used for grabbing and holding objects, as are the finger tips. This lack of use by the forearm makes it less likely that the lanced site will be irritated or injured due to the activities performed by the body site.

The elevated annular lip 120 defines a recessed area that is disposed radially inwardly of the annular lip.

Within this recessed area is a skin distancing member that includes a recessed dish 125 surrounded by a lip and platform 127 on which the body part can be placed. The skin distancing ring member 124 is disposed concentrically with the pressure cup annular lip 120. The skin distancing ring member 124 is sized and positioned so as to maintain the body part, and preferably the skin of the body part at an appropriate position relative to the capillary portion of the device 10. More particularly, the recessed annular skin distancing lip 127 and recess 125 help to keep the skin above the centrally disposed central aperture 130, so that the user's skin does not plug (close) the aperture, which is the inlet to the capillary portion of the device 10.

A central aperture 130 is centrally disposed within the body part engaging surface 20, and is surrounded by a raised central dome 126. The central aperture is sized and positioned for not only receiving blood flowing there through into the capillary portion of the device, but also to receive the tip 27 of the lancet 24, so that the lancet tip 27 may penetrate the skin of the user, to cause blood to flow out of this punctured skin site.

Figure 8:
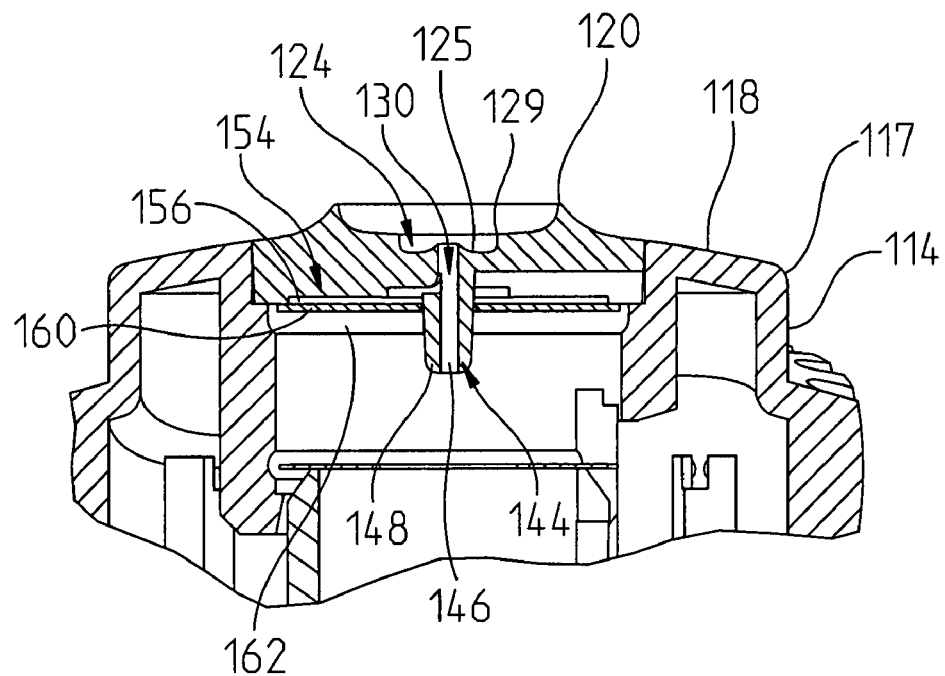
FIG. 8 is an enlarged sectional view of a portion of the support member.
Figure 9A:
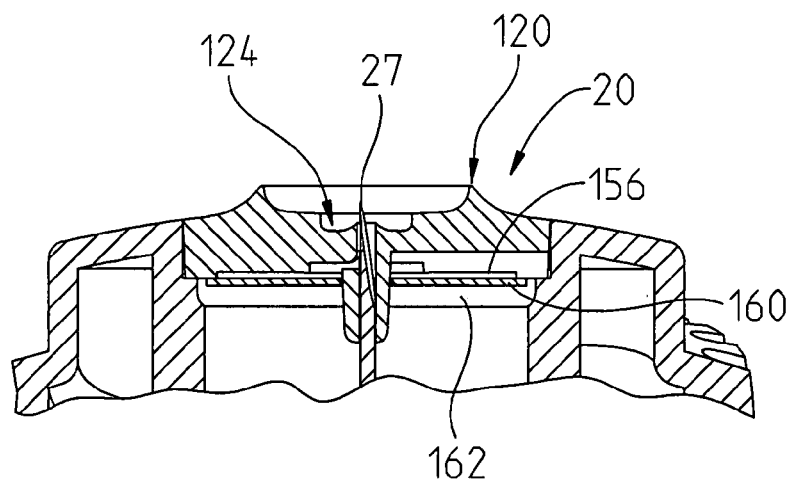
FIG. 9A is a sectional view, similar to FIG. 8, except showing the lancet in the piercing position.
Figure 9B:
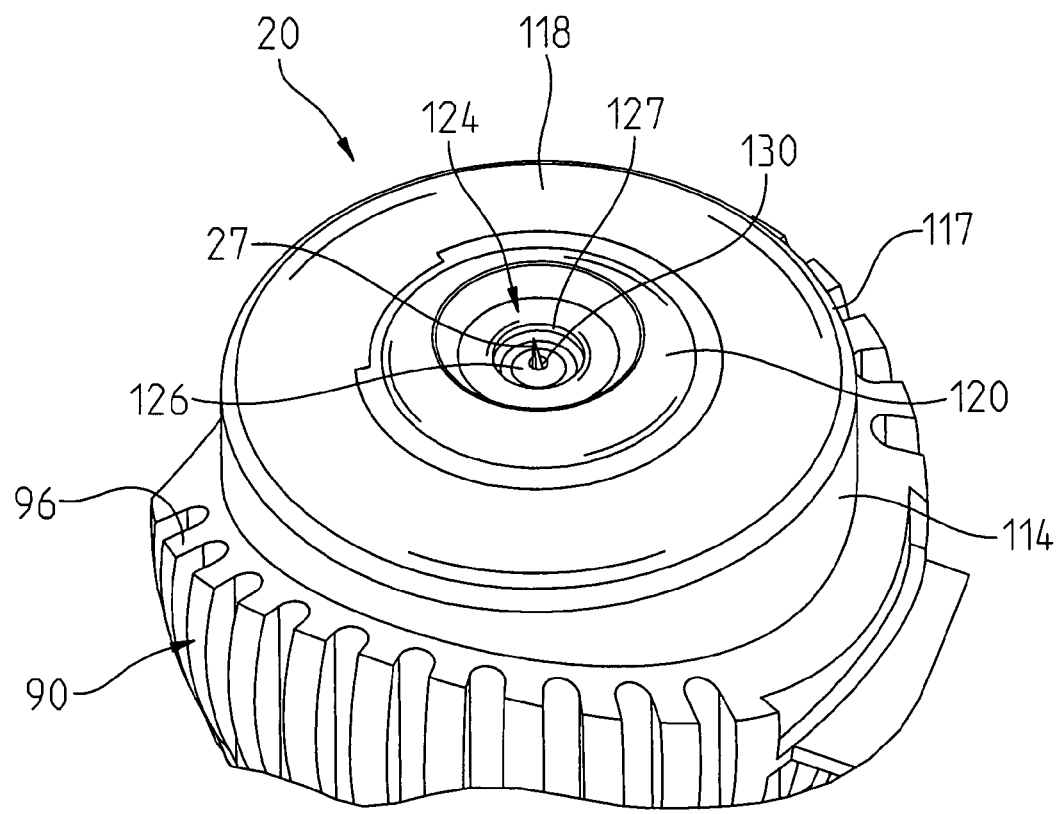
FIG. 9B is a partial, perspective view of the body part engaging surface showing the lancet extending there through in the piecing position.
Figure 9C:
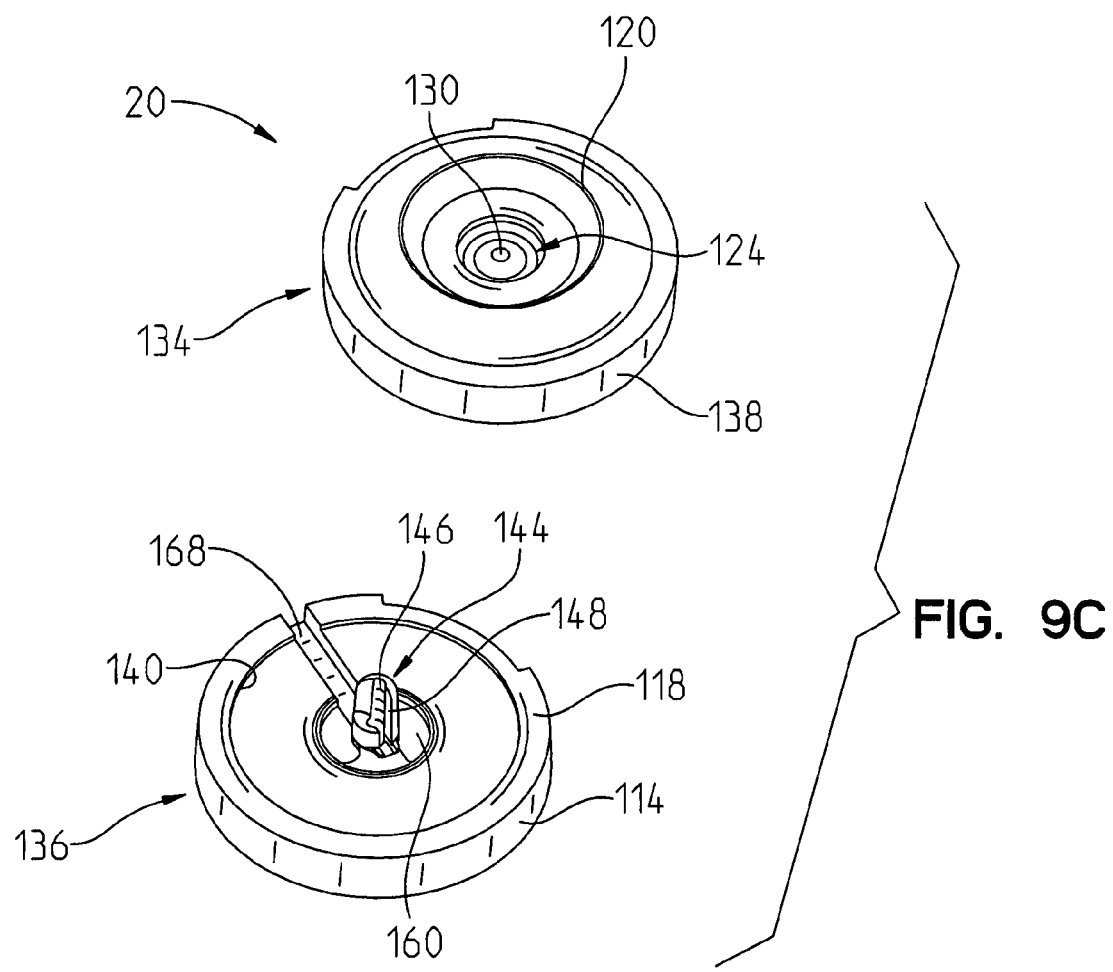
FIG. 9C is an exploded view of the upper and lower members of the body part engaging surface of the present invention.
Figure 9D:
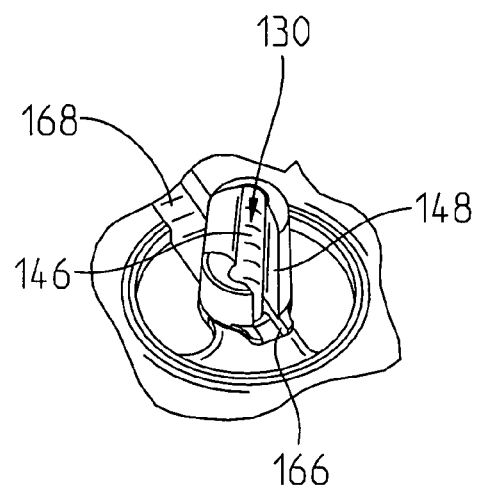
FIG. 9D is a partial view of the capillary member of the present invention.

Turning now to FIGS. 8, 9C and 9D, the body part supporting surface 20 is preferably comprised of separately formed components, including an upper member 134, and a lower member 136. The primary purpose served by the upper member 134 is to provide a body support surface upon which the user can place the body part such as a finger, or forearm that is to be lanced, so the blood can be drawn therefrom for testing. To that end, as discussed above, the upper member 134 includes the pressure cup 120 and the skin distancing member 124.

The lower member 136 serves the function primarily of serving as a test member support, and it contains the capillary mechanism and test member mechanism thereon.

The upper member 134 includes a radially outwardly facing cylindrical side wall 138 that is sized and positioned to be placed in an opposed relation, so that it is interiorly received by the radially inwardly facing side wall 140 of the lower member 136. The lower member 136 includes a centrally disposed axially extending capillary tower 144. The central aperture 130, that extends through the upper member 134, actually opens downwardly in the tower 144 as a centrally disposed passageway, that includes a central portion 146, and a radially outwardly disposed portion 148. The centrally disposed portion 140 comprises the channel through which the lancet passes through the upper 134 and lower 136 members, so that the tip 27 of the lancet can extend above the central dome 126 (see FIG. 9B) so that it can pierce the skin of the user so that blood may flow from the lanced site.

Additionally, blood flows through the central portion 146 in the radially outwardly disposed portion. During the flow of the blood through the central and radially outwardly disposed portions, the plasma component of the blood starts to become separated from the cellular components of the blood. This separation of the plasma from the cellular componnents is a separation required for many blood assay tests, and that is described in more detail in the Kloepfer et al., patents, and published applications discussed above, and that are incorporated herein by reference.

The tower 144 is disposed within a centrally disposed well 152 that surrounds the tower 144. Within the well 152 are placed test member components 154. The test member components 154 include a radially extending capillary space 156, that also serves as a suction chamber. The capillary space 156 represents a space into which blood can flow so that the appropriate components of the blood (usually the plasma components) will be able to interact with the reagents contained on the reagent containing disk shaped test member disk 160, that defines the lower wall that defines the capillary space 156. A test member support 162, that can also serve as a calibration component (See FIG. 6) is disposed below the reagent containing test member 160.

The test member 160 can include one or a variety of reagents. Several well known test member reagents exist, that can be employed to determine the presence, or either semi-quantitatively or quantitatively measure the amount of a particular component, or sets of components in a body fluid sample. Examples of reagents that can be placed on the test member to perform these tests can be found in patents held by the companies who manufacture such test member products, including Bayer, AG, and Roche Diagnostics.

The path through which the blood flows will be discussed in more detail below, but before leaving this area, it should be noted that a foot member 166 is placed at the base of the radially outwardly disposed portion 148 of the central channel 130, (FIG. 9D) to provide a transition and guide to the blood flowing from the channel 148, and into the capillary space 156.

The foot member 166 should be in contact with the upper surface of the reagent containing test member 160 to facilitate this type of blood flow. A radially extending air vent channel 168 extends between the base of tower 144, and the radially outer edge 114 of the lower member 136. The air vent channel 168 provides an air vent to permit the flow of fluid radially outwardly in the capillary space 156 to proceed, without being hindered by air pressure considerations that would exist if no vent were present.

Figure 11:
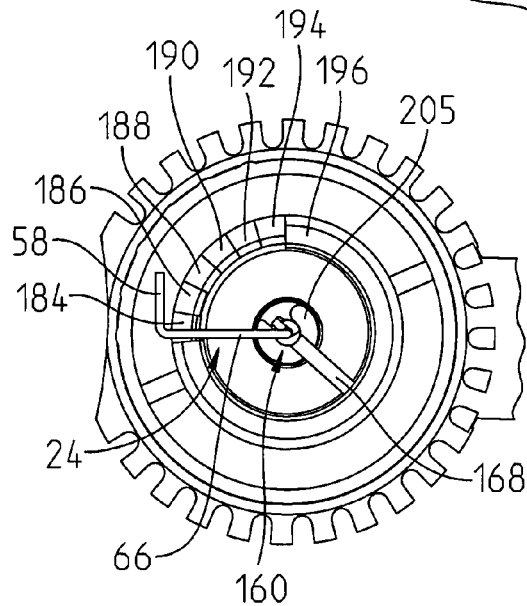
FIG. 11 is a bottom view of the present invention showing the test member without any reactant product thereon.

As best shown in FIGS. 7 and 11, the underside surface of the support member 18 includes a downwardly opening cup member 172, that is generally cylindrical in configuration, and includes a radially outwardly facing, axially extending outer wall surface 174, and a radially inwardly facing axially extending inner wall surface 176. The purpose of the wall surfaces of the cup member 172 are to fit between the upstanding support guide member 54 of the body member, and the outer wall 48 of the cylinder 46 of the body member.

The outer wall 174 of the inner cup 172 is placed in an opposed relationship to the radially inwardly facing wall of the support member 54, and the radially inwardly facing wall 176 of the support cup 172 is placed in an opposed adjacent relationship with the outer surface 48 of the cylindrical support tube 46.

The support cup 172, support/guide member 54 and cylindrical tube 46 are sized and positioned, so that the support cup 172 is slideably received by the body member, and is positioned so that the support member 18 and body member 14 are disposed generally coaxially with each other, and are positioned to be slideable with respect to each other, so that the support member 18 and body member 14 can move between an expanded and compressed position.

Figure 12:
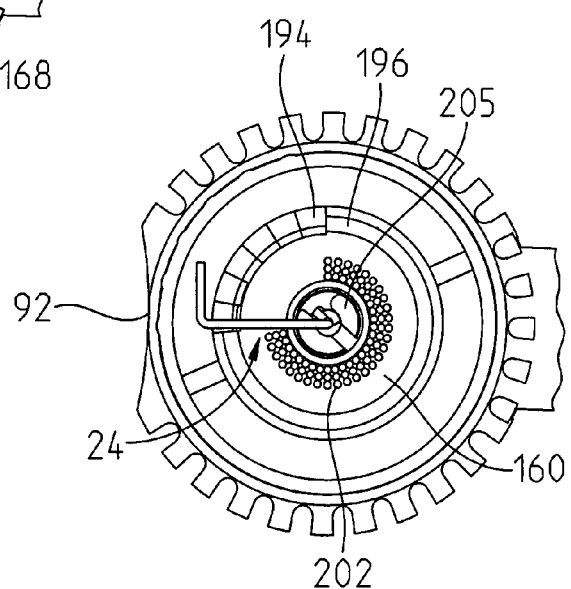
FIG. 12 is a bottom plan view similar to FIG. 11, except showing reactant product thereon.
Figure 22:
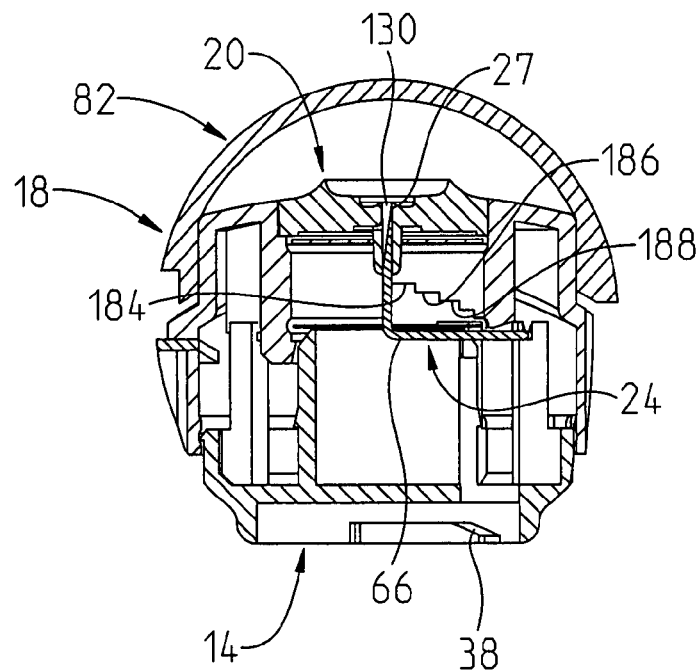
FIG. 22 is a sectional view of the device showing the body and support member in their respective first or "expanded" positions with respect to each other, and the lancet in its storage position.

The support cup 172 also includes an axially outwardly facing, radially extending end surface 180, that includes an adjuster member, that permits the user to adjust the distance that a tip 27 of the lancet 24 (FIG. 9A), is allowed to extend above the body surface 20. The adjuster member 182 comprises a series of five axially offset "step" surfaces, that are placed at a level different than the general surface 194 of the end surface 180. As best shown in FIGS. 11, 12 and 22, the five axially offset surfaces 184, 186, 188, 190 and 192 are arranged in stair-step fashion, from the first axially offset surface 184, which is the "highest" surface, to the lowest surface 194 which actually does not constitute a step, but rather, constitutes just a continuation of the remainder of the end surface. It will be appreciated that the height of the five axially offset surfaces 184-192 differs from the normal end surface 194.

Figure 24:
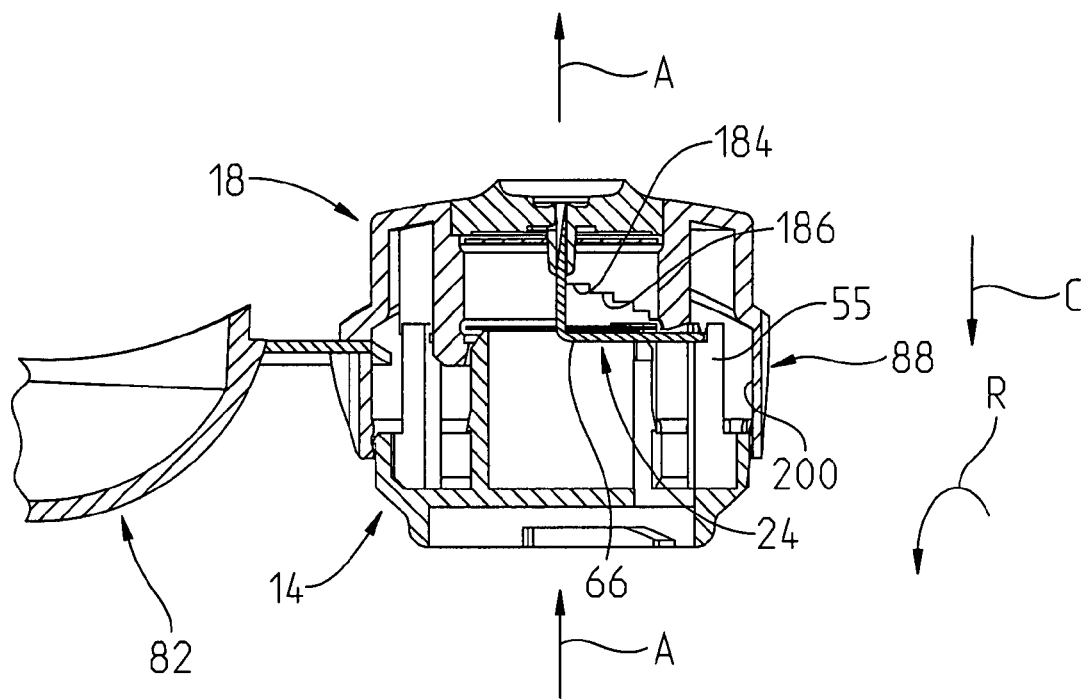
FIG. 24 is a sectional view similar to FIG. 22, except showing the cap in the open position.

Turning now to FIG. 24, the axial movement of the support member 18 relative to the body member 14, in a direction indicated generally by arrow C, causes the axially offset steps 184-194 to move downwardly, toward the radially extending arm 66 of the lancet 24, when the lancet 24 is in its storage position. The lancet 24 is in its storage position normally before the device is used to perform a test. As the support member 18 continues to move axially downwardly, it will reach a point where one of the axially offset steps 184-194 eventually engages the laterally extending arm 66. Just prior to this engagement of one of the offset surfaces 184-194, the lancet is in a position similar to that shown in FIG. 27 where the tip 27 of the lancet 24 is disposed above the upper body part receiving surface 20 of the test member 10. When the lancet tip 27 is in this position, it is capable of piercing the skin of the user.

The user can determine which of the various offset surfaces 184-194 is chosen to engage the radially extending leg 66 of the lancet 24. This adjustment is affected by rotating the support member 18 relative to the body member 14 about the shared axis A of the support member 18 and body member 14. By rotating the support member 18, one can position the desired offset surface 184-194, above the lancet's 24 radially extending leg 66, so that the desired surface 184-194 strikes the lancet's 24 radially extending leg 66. If the user chooses to strike the lancet leg 66 with the first or highest step 184, the tip 27 of the lancet 24 will extend a relatively greater distance above the body surface, and hence pierce the skin of the user to a greater distance or depth, than will occur if the user positions the support member so that the lancet leg 66 is engaged by the sixth or lowest offset surface 194.

By making this adjustment, the user can determine the depth to which the lancet 24 tip 27 pierces the skin. Preferably, the lancet 24 pierces the skin to a sufficient depth to enable a sufficient amount of blood to flow out of the lanced site, so that enough blood is available for completing a test. On the other hand, the lancet should penetrate the skin to the minimal depth necessary to achieve this blood flow, because by minimizing the depth, the user also tends to minimize the amount of pain that is associated with a lancet "stick".

By rotating the support member 18 so that it is positioned so that one of the intermediate surfaces 186-192 strikes the radially extending leg 66 of the lancet, the lancet tip 27 would be allowed to penetrate an intermediate distance somewhere between the relatively greater distance it would penetrate if the first step 184 were selected, and the relatively smaller and shorter depth that it would penetrate if the lowest offset surface 194 is chosen.

Figure 28:
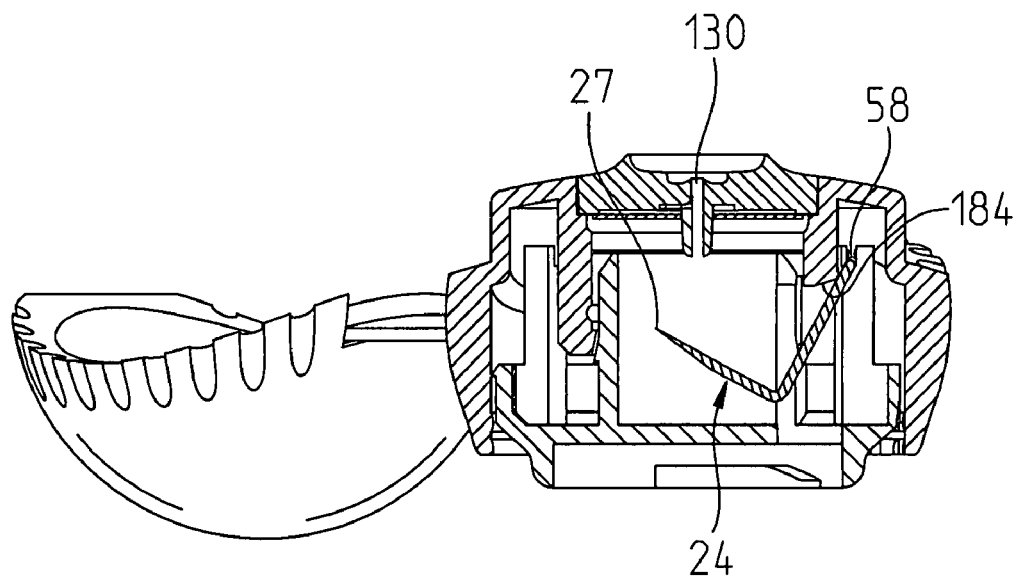
FIG. 28 is a sectional view, showing the lancet in the partially retracted position.

As will be described in more detail later, after the offset surface 184-194 strikes the radially extending leg 66, the lancet is pivoted in a direction indicated generally by arrow R of FIG. 24, on its pivotal connection with the lancet support 55, to move downwardly and into the retracted position, such as is shown in FIGS. 28 and 29.

It will also be noted that the radially inwardly facing surface 200 (FIG. 24) of the exterior wall 88 of the support member 18 engages and is placed in an opposed relationship with the cylindrical perimetral base wall 42 of the body member 14, to further aid in properly positioning the support member 18 on the body member 14, so that the body member can move axially relative to the body member 14 between the expanded and compressed positions.

The readers attention is now directed to FIGS. 11 and 12. FIGS. 11 and 12 are views through the bottom of the body member. As discussed above, the interior of the device is generally hollow, as is the base 34. This hollowness enables one to look up the hollow interior, to see the reactant product that forms on the reactor area 205 of the test member 160 from the reaction between the reagents contained on the test member 160 and the body fluid that is placed thereon. Preferably, the reaction between the reagents and the compound(s) of interest in the blood will form a colorometric reaction, wherein the reaction product produced is a colored reaction product, wherein the color bears some relationship either to the particular chemical of interest found on the test member, or otherwise, to the quantity of the particular chemical (e.g. glucose, cholesterol) of interest on the test member. Illustrated dots 202 shown in FIG. 12, can be "calibration" dots that are placed on the calibration member 162.

The calibration dots 202 can be pre-printed to replicate various colors, corresponding either to various compounds, or else, various quantities of compounds. These calibration dots 202 can also comprise a type of "bar code" that contains identifying information about the test device 10. The colors formed by the reactant product colors from the reaction of the reagent and the test fluid are placed adjacent to the calibration color dots 202, so that their color can be better compared, both by the meter, and by a visual check. By comparing the colors, one would likely get a more accurate and reproducible reading of the quantity of the test compound of interest formed by the interaction of the compound with the reagent on the test member 160.

The manner in which the device moves the lancet 24 between its storage position and its retracted position is well illustrated by reference to FIGS. 13-17.

Turning first to FIG. 16, it will be noted that the lancet 24 when in the storage position, has its proximal end 68 pivotably coupled to lancet support member 55, and has its radially extending leg 62 positioned to rest on the resistant shelf 73 of the cylinder 46.

The relative dimensions of the diameter of the lancet 24, and the width of slot 72 will cause the radially extending leg 66 of the lancet 24 to rest upon angled shelf 73, and not move axially through slot 72, unless some force is exerted on the lancet 24 to push it downwardly.

The dimensions of slot 72 are chosen so that the amount of force required to push the radially extending leg 66 of the lancet through the slot 72 is a greater amount of force than is normally required to enable the tip 27 of the lancet 24 to penetrate the skin of the user. As such, the shelf 73, wall 75 and slot 72 cooperate to provide enough resistance in the movement of leg 66, so that the lancet tip 27 will pierce the skin before moving into its retracted position.

Figure 13:
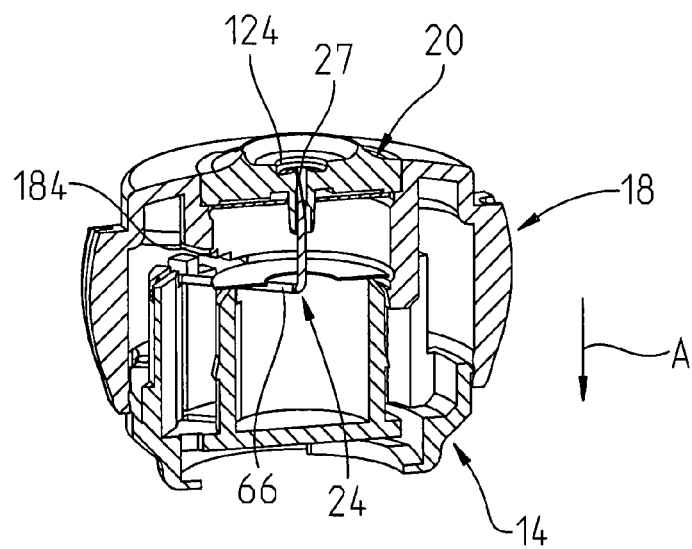
FIG. 13 is a sectional view of the support member and body member, showing a lancet in a piercing position.

Turning now to FIG. 13, the lancet 24 is shown at a position, just prior to one of the axially offset surfaces 184, engaging the radially extending leg 66 of the lancet.

At this point, the support member 18 still can move an additional distance downwardly, in a direction indicated by arrow A to "compress" the support member 18 and body member 14. It will also be appreciated that the tip 27 of the lancet 24 lies just below the body part receiving surface 20 (and just below the inlet of capillary portion 130), and that further movement of the support member 18 in a direction indicated by arrow A, will cause the tip 27 of the lancet to extend above the surface 20, so that it will be positioned above the body part engaging surface, similar to the position shown in FIG. 9B.

Figure 14:
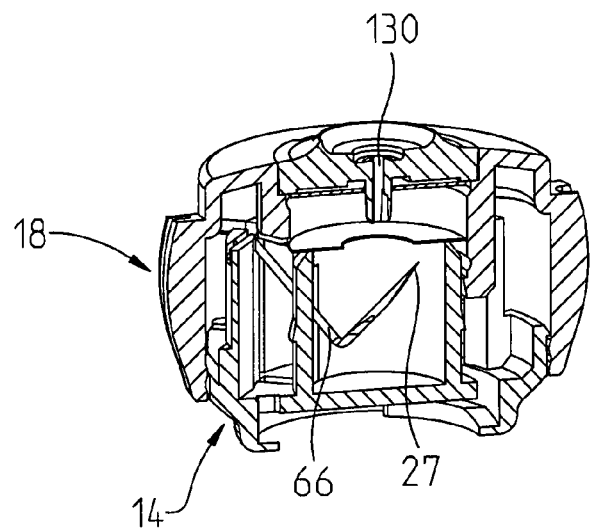
FIG. 14 is a sectional view of the body member and support member showing the lancet in the partially retracted position.

Turning now to FIG. 14, it will be noted that the support member 18 has moved axially downwardly on the body portion 14, when compared to the position shown in FIG. 13. In this position, one of the axially offset surfaces 184 has already engaged the radially extending leg 66 of the lancet 24, and has caused the lancet 24 to pivot downwardly, to a position where the tip 27 is removed from aperture 130.

Figure 15:
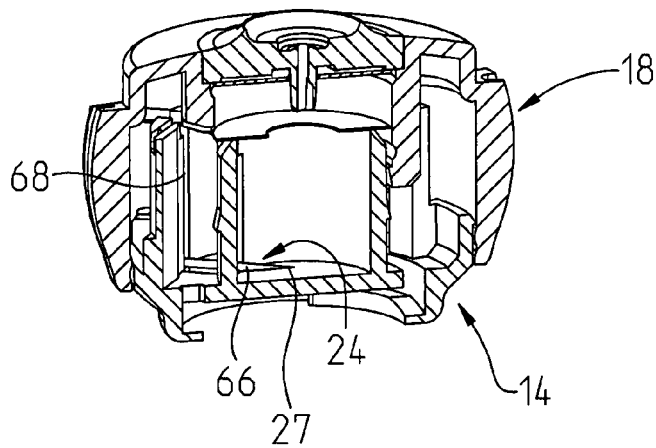
FIG. 15 is a sectional view of the body member and support member, showing the lancet in the fully retracted position.

In FIG. 15, a support member 18 is shown in its second or fully compressed position vis-a-vis body member 14, so that the lancet 24 is in its fully retracted position, wherein the distal leg 68 of the lancet is generally disposed radially, and the tip 27 lies generally near the bottom of the body member 14. In this position, the lancet 24 is safely tucked interiorly of the body member 14, in a position where it is highly unlikely to travel outside the testing device 10, and therefore, is highly unlikely to be a in a position where it can accidentally stick the user, or another person.

Figure 18:
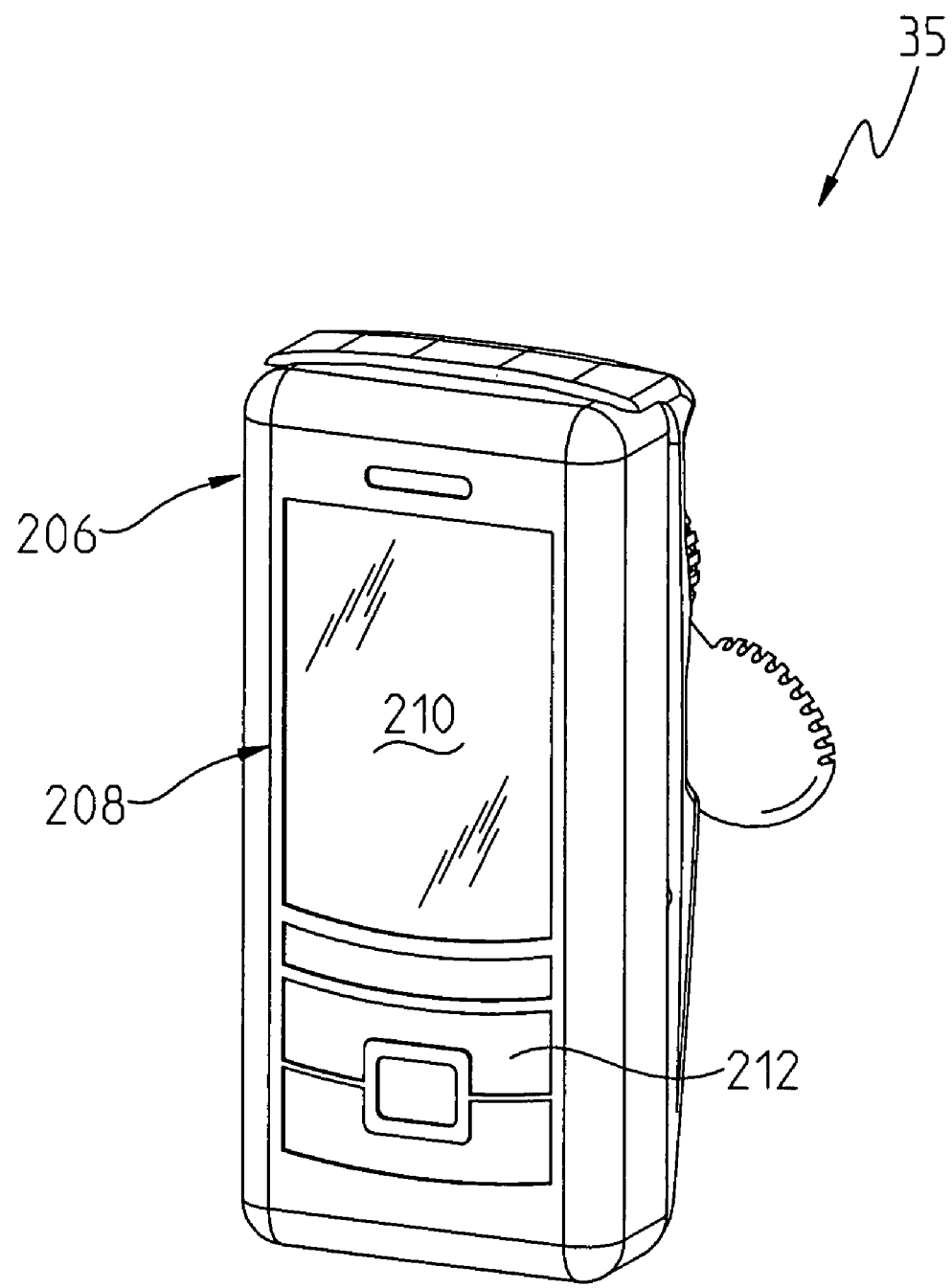
FIG. 18 is a front view of a cell phone-type meter that can be used with the testing device of the present invention.
Figure 19:
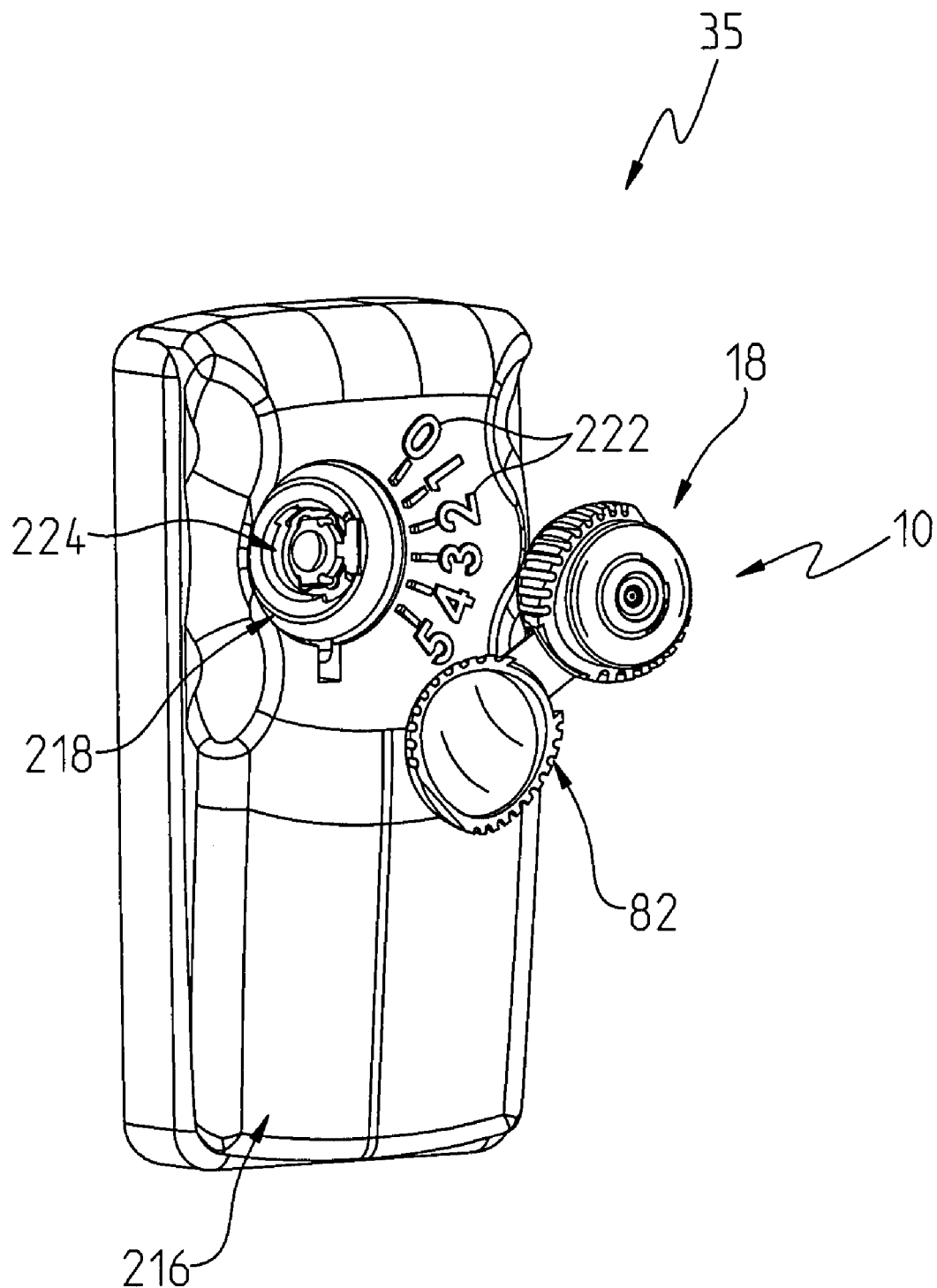
FIG. 19 is a rear perspective view of the cell phone-type meter of the present invention showing the mounting member of the cell phone to which the testing device mounts.
Figure 20:
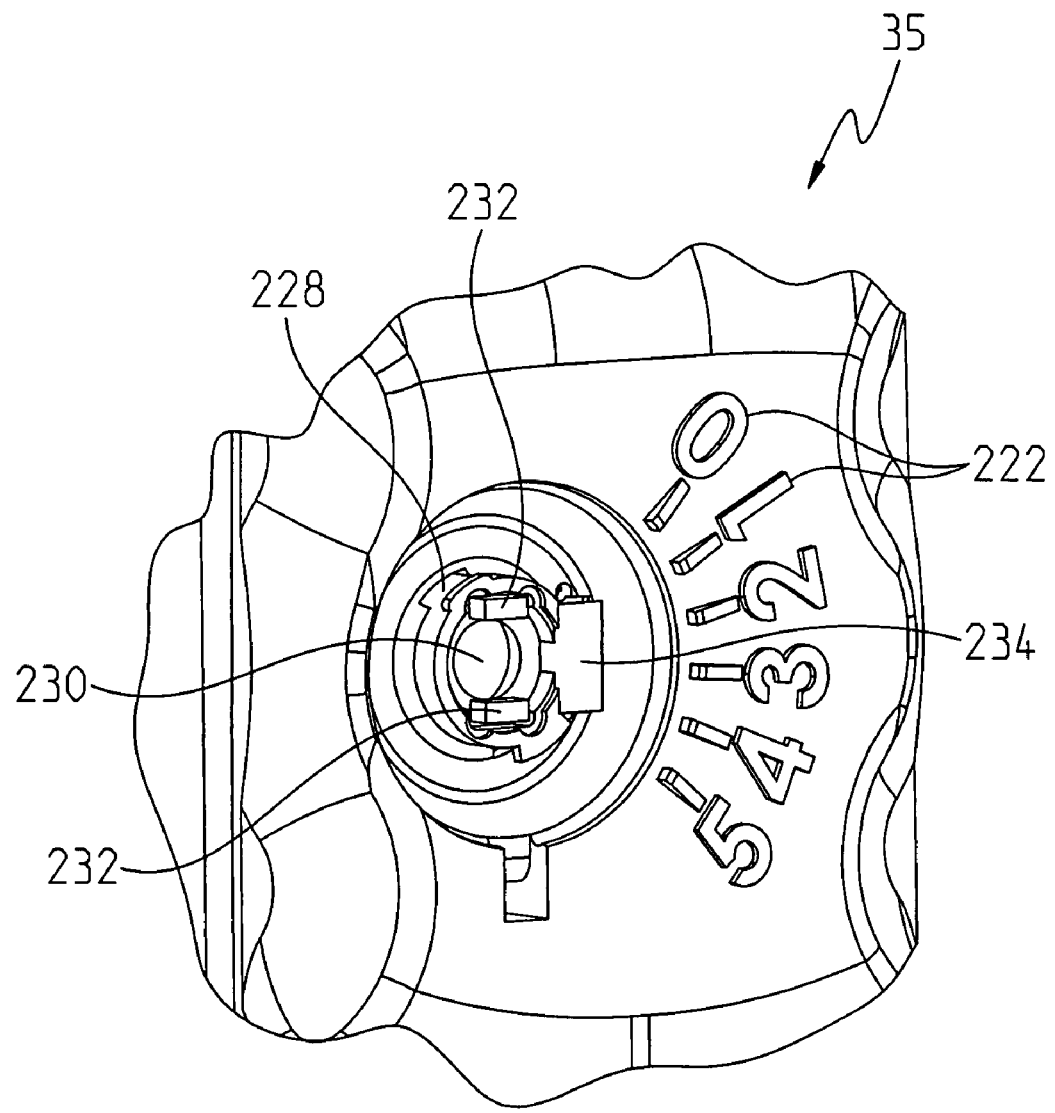
FIG. 20 is an enlarged view of the mounting member of the meter.

A meter 35 with which the testing device is designed to be used, is shown best in FIGS. 18-20. The meter 35 includes a case 206 that houses all of the internal components (not shown) of the meter 35. The meter 35 is shown as being a cell phone-type meter, that has dual functionality insofar as it can be used as a cell phone, and also as a test meter. One benefit of this, as explained in the Kloepfer cell phone patent application above, is that most cell phones contain a camera system already, that can be used to "read" colorometric reactions that occur on the reagent test member 160 of the device, and processing capabilities that can be exploited.

The front of the cell phone/meter 35 includes a screen 210 upon which information can be displayed, that preferably comprises a touch-type screen that also enables commands to be given through touching appropriate places on the screen 210. A button-laiden control panel 212 also appears on the front surface for permitting the user to enter commands to the cell phone/meter 35.

Turning now to FIG. 19, the rear of the cell phone/meter 35 is shown as including a case member 216, and a testing device receiver/coupler 218. A series of depth indicia, here shown as 0, 1, 2, 3, 4 and 5 (222) are formed on the rear case member 216, to indicate the depth at which the testing device has set the lancet 24. Contained within the receiver/coupler are a variety of meter components.

As shown in FIG. 20, the meter components contained within the test receiver include a bayonet mounting surface 228, for receiving the bayonet mount formed in the base 34 of the testing device 10. One or more LEDs 232 are provided for serving for as a light source, to light up in a controlled manner, the interior of the testing device 10, adjacent to the test member 160, so that enough light will be present to enable the meter or camera to perform its function. A switch 234 is also operatively coupled in this area to detect the presence or absence of a testing device 10 on the receiver/coupler 218.

Figure 21:
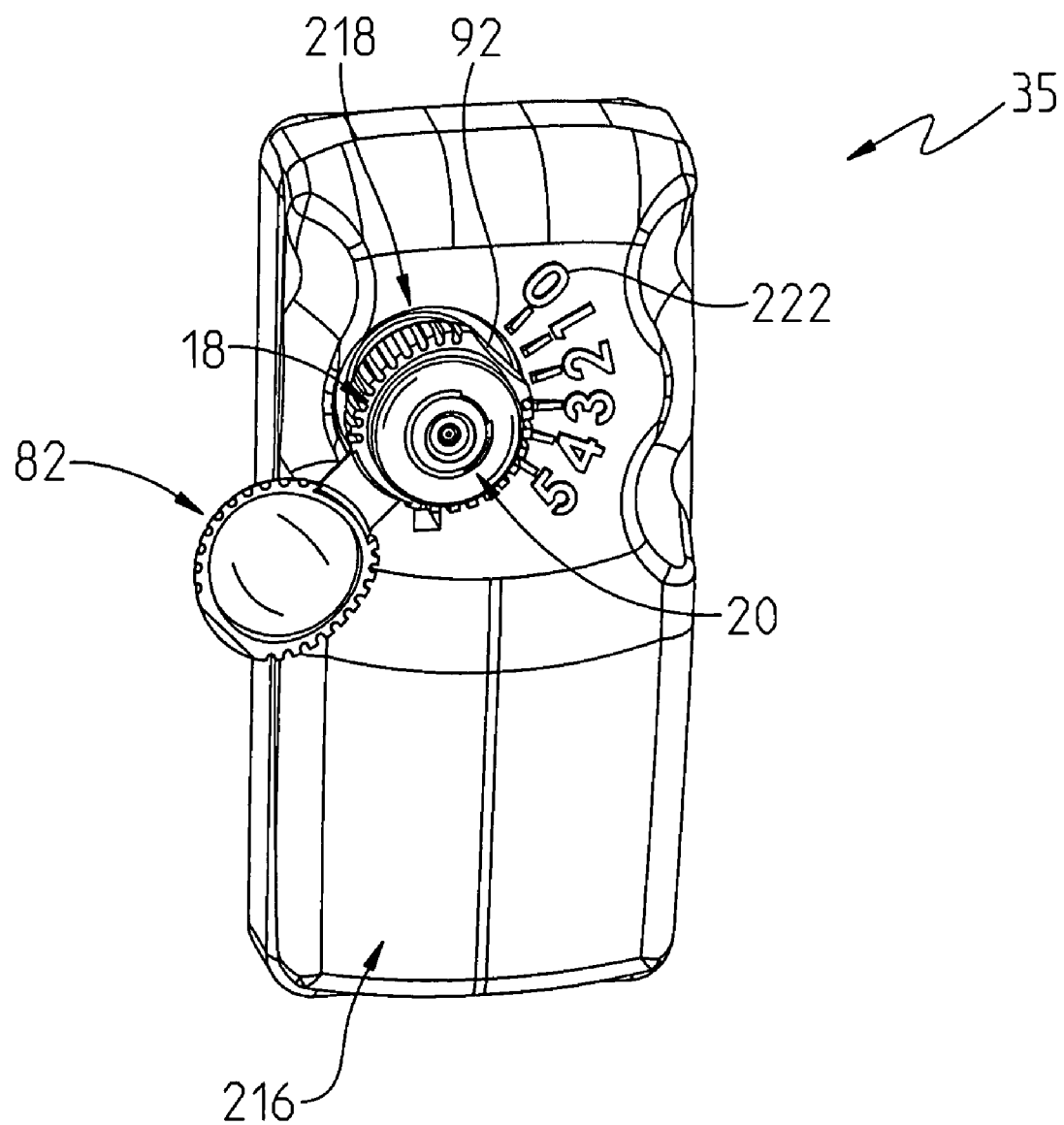
FIG. 21 is a rear perspective view showing the testing device mounted upon the cell phone-type meter of the present invention.

Turning now to FIG. 21, a testing device 10 is shown as being mounted, through the respective bayonet mounts, to the receiver/coupler 218.

It will be noted that the concave surface 92 of the support member is placed opposite the "zero" indicia 222. This placement of the concave surface 92 adjacent to the zero indicia, can indicate to the user that the lowest axially offset step 194 will be used so that the lancet 24 tip 27 will penetrate the skin, the smallest distance available by the unit.

If the concave member 92 were pointing to indicia 5, which would occur if the support member 18 were rotated about its axis, so that the concave surface 92 faced indicia 5, it would indicate that the highest axially offset surface 184 of the adjuster was being employed, so that the lancet tip 27 would penetrate the greatest possible distance into the skin of the user. It will also be appreciated that if the user desired to set the lancet tip 27 depth at an intermediate level, he would cause the center of the concave surface 92 to point to one of the intermediate indicia, such as 1, 2, 3 or 4.

In this position, the user can place his finger over the body part receiving surface 20 to begin the testing procedure.

The reader's attention is now directed to FIGS. 22-28, that depict the sequence that the lancet goes through, in moving from its storage to its retracted position.

Turning first to FIG. 22, a sectional view of the device is shown. It will be noted that the lancet 24 has its radially extending leg 66 disposed in a radially extending direction, and that the tip 27 of the lancet is disposed below the body part receiving surface 20, and below the tip of the inlet 130 of the capillary portion. It will also be noted that the axially offset surfaces 184, 186, 188 are above, and have not yet engaged the lancet 24.

Figure 23:
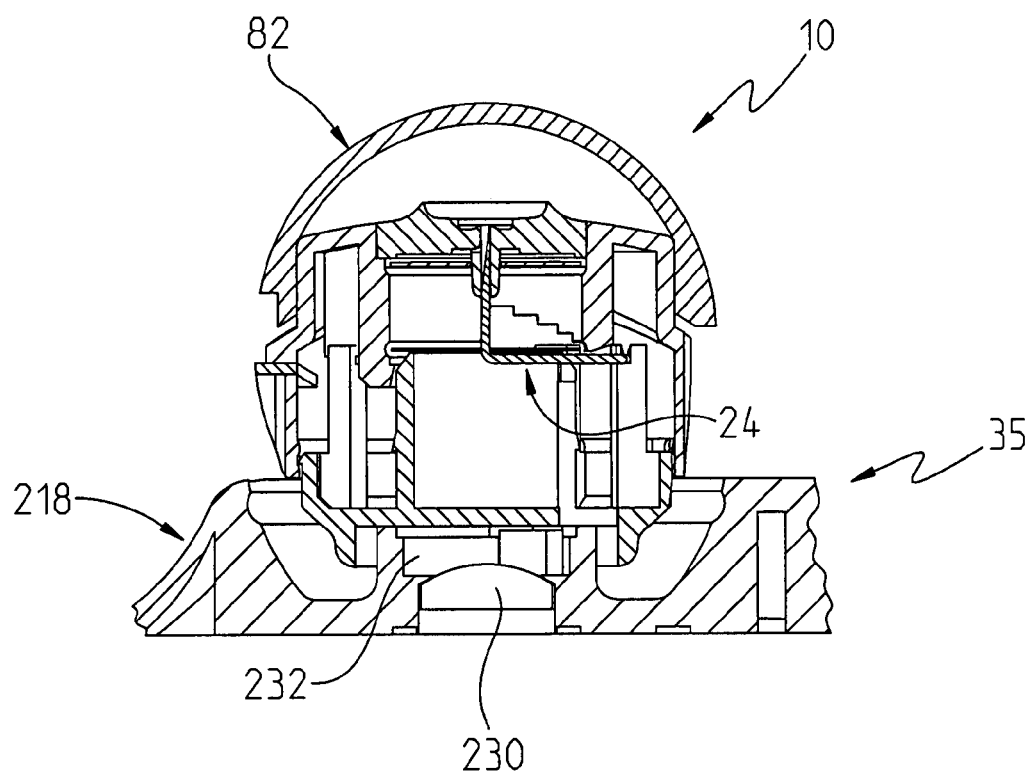
FIG. 23 is a sectional view similar to FIG. 22, except showing a testing device being coupled to a meter useable with the present invention.

In this position, the support member 18 and body member 14 are in their first, or storage position, where they are "expanded" relative to each other and not compressed. FIG. 23 shows a view similar to FIG. 22, with the exception that the device 10 is shown as being coupled to the receiver/coupler 218 of cell phone/meter 35.

Figure 25:
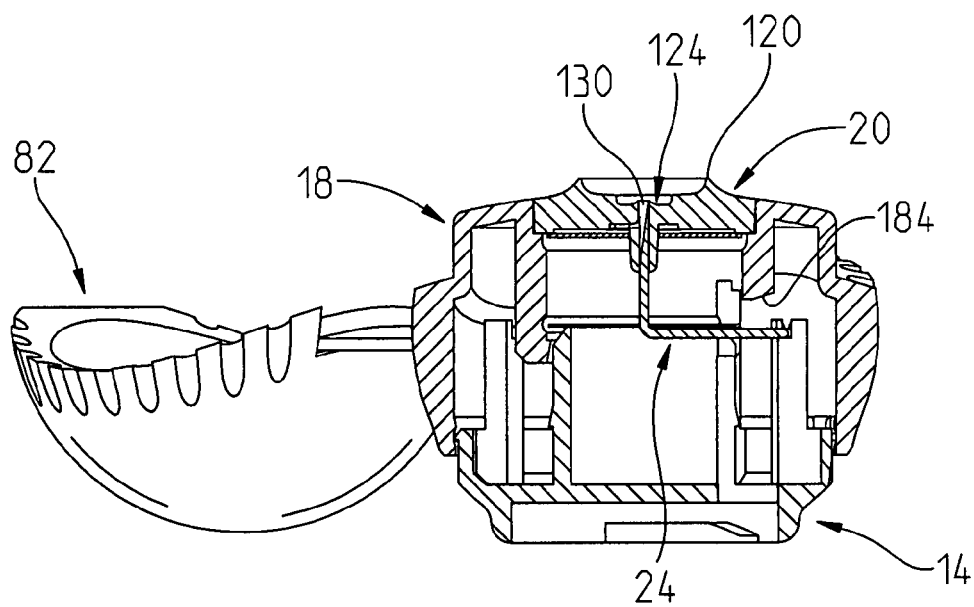
FIG. 25 is a view, similar to FIG. 24, except showing the base, rotated approximately 60 degrees from the view shown in FIG. 24.

FIGS. 24 and 25 also show the device in the storage position, similar to FIGS. 22, except that FIG. 24 shows the cap 82 in an open position, and FIG. 25 shows the device rotated about 45 degrees about its axis, from the position shown in FIGS. 22, 23 and 24.

Figure 26:
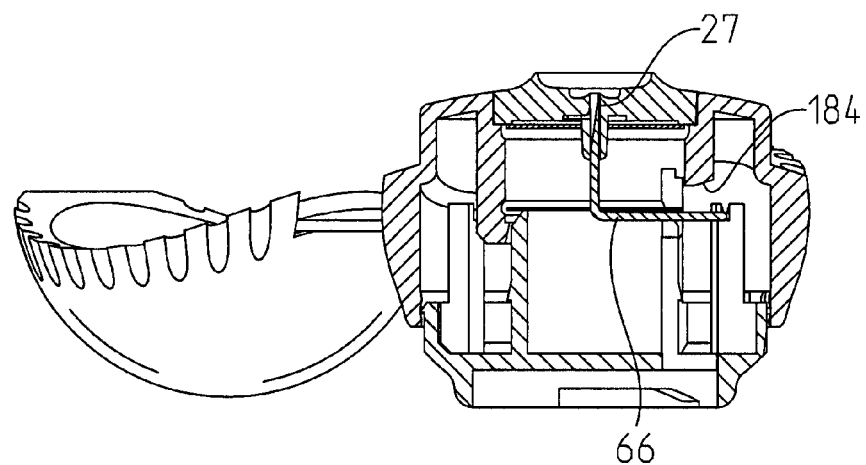
FIG. 26 is a view, similar to FIG. 25.
Figure 27:
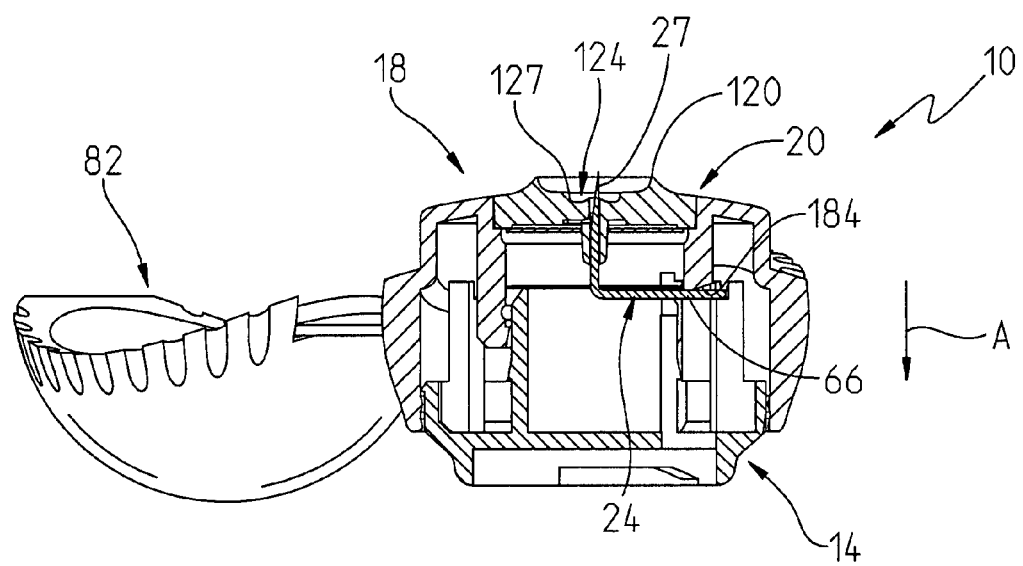
FIG. 27 is a view showing the lancet in its piercing position, with the body member and support member moved between the first (fully expanded) and second (fully compressed) positions, to reside in an intermediate position.

FIG. 26 shows a view generally similar to FIG. 25, and FIG. 27 shows a view, wherein the support member 18 has moved in an axially compressed direction, which direction is indicated generally by arrow A. FIG. 27 shows the device 10 wherein the lancet 24 is in the piercing position, as it will be noted that the tip 27 of the lancet 24 is extending above the body part receiving surface 20, and in fact, the tip 27 of the lancet 24 is about at the same level as the lip of the pressure receiving cup 120, and is above the level of the lip 127 of the skin distancing member 124.

It should also be noted that the lancet engaging axially offset step 184 is just about to engage the radially extending leg 66 of the lancet. This contrasts from the view of FIG. 26 where it will be noticed that the lancet engaging surface 184 is positioned above the radially extending leg 66 of the lancet.

FIG. 28 shows the lancet 24 after it has begun moving toward its retracted position. It will be noted that tip 27 of the lancet 24 is completely removed from the capillary channel 130, and the lancet engaging surface 184 is positioned below the pivot point (leg) 58 of the lancet 24. FIG. 29 shows the lancet 24 in the fully retracted position wherein the radially extending leg 66 of the lancet extends in a generally axially direction.

Figure 30:
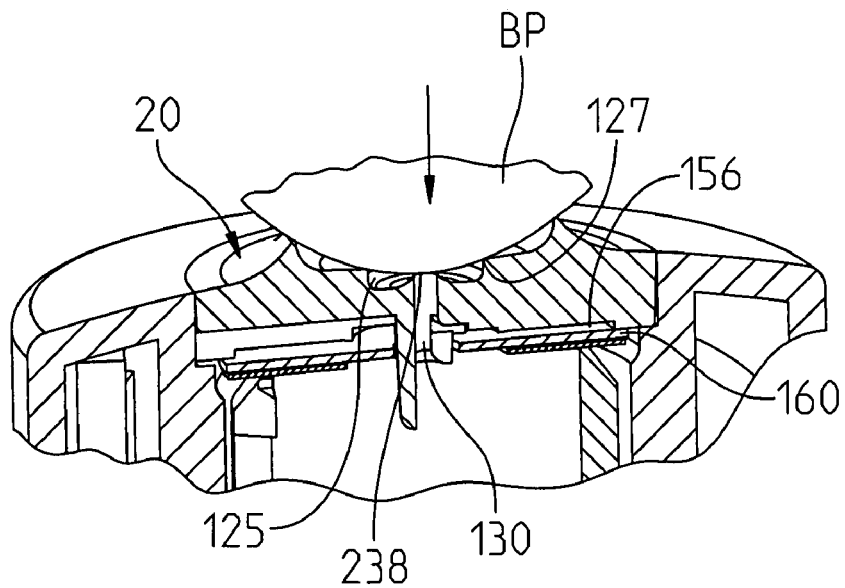
FIG. 30 is a sectional view showing the path of the blood flow, prior to the blood engaging the capillary mechanism of the present invention.
Figure 31:
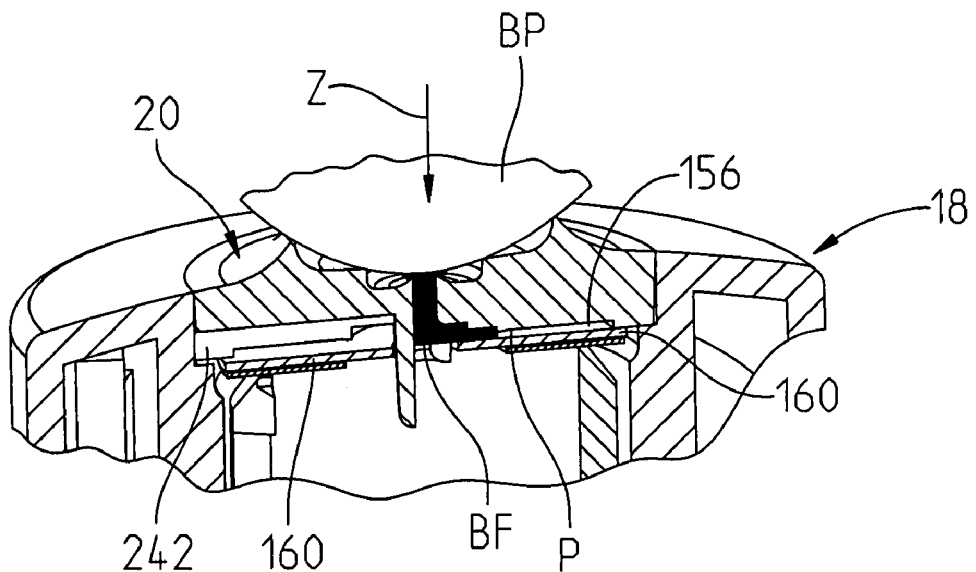
FIG. 31 is a view similar to FIG. 30, showing the path of blood flow through the capillary member of the present invention.
Figure 32:
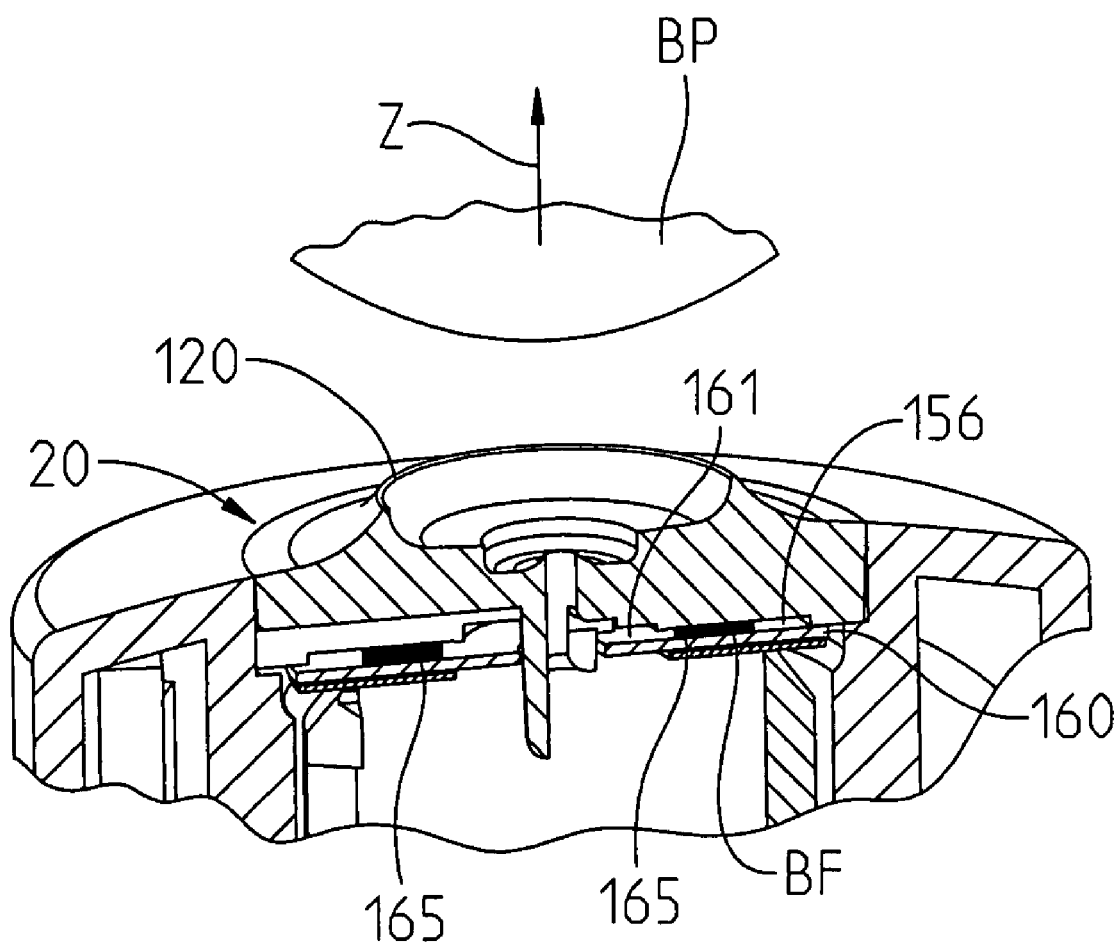
FIG. 32 is a sectional view, similar to FIG. 31.

The reader's attention is now directed to FIGS. 31 and 32, that illustrate the sequence of events that occurs relating to the capillary channel during the use of the testing device 10. A body part BP is shown as being placed in FIG. 30 on the body part receiving surface 20. The skin of the fingers straddles the lip 127 of the body distancing member 124, with the recess 125 of the body distancing member providing enough space so that the finger does not plug the inlet opening 238 of the capillary channel 130.

In FIG. 1, the arrow Z shows pressure being exerted downwardly on the body part supporting surface 20. This pressure is the pressure that will cause the support member 18 to compress the testing device 110, and cause the lancet tip 27 to travel to its piercing position. FIG. 31 assumes that the piercing has already occurred, and that a body fluid BF such as blood has begun to run out of the body part finger BP, and has begun flowing axially into the capillary channel 130, and radially outwardly, in the capillary space 156 that is above the test member 160.

It is important to note that the suction area 156 is pinched off at pinch point P against the testing disk 160. Pinch point P pinches off the capillary channel/suction area 156, due to the force that is exerted by the finger, that causes the peripheral area 242 of the body part supporting surface to press downwardly on the test disk 160 to cause the test disk 160 to bend, to thereby form the pinch point P.

Figure 10:
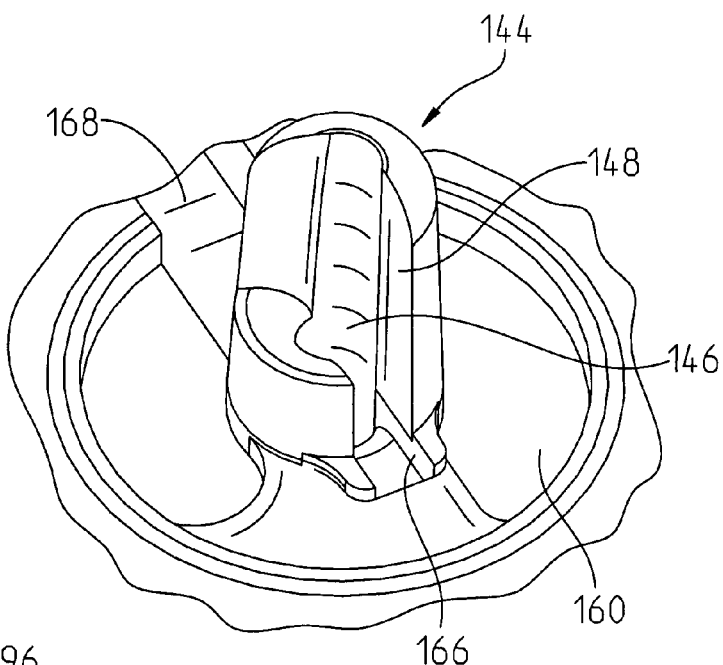
FIG. 10 is a perspective and partly broken away view of the capillary and test member of the present invention.

This pinching prevents the radial movement of the body fluid past the pinch point P. Turning now to FIG. 32, arrow Z shows that the pressure of the body part has been lifted off the body part receiving surface 20. This removal of force from the body part receiving member 20, enables the test disk 160 to straighten out, which enables the capillary channel 156 to leave its pinch point. This removal of the pinch point, when coupled with the venting achieved by the vent channel 168 (FIG. 10), fosters capillarity, and fosters the radially outward movement of the body fluid BF.

Left behind (upstream from) the main bolus of body fluid BF, is the radially inward area 161, which is the reaction capillary compartment of the test disk 160, The reaction capillary compartment 161 contains the body fluid that has reacted with the reagent, to form the reactant product. This reaction capillary compartment 161 is the area in which the meter focuses its attention (e.g. the camera takes its picture) to obtain a reading of the test disk. It will be noticed that he main bolus of excess blood BF has traveled downstream of the reaction capillary compartment to the excess blood capillary compartment 165

Capillarity is fostered because air is drawn into the capillary chamber, that brings oxygen into the chamber 156, which is necessary for some of the reagent/plasma reactions to occur, along with fostering the flow of blood radially outwardly. Additionally, there exists a capillary force differential between the reaction capillary compartment 161 and the excess blood capillary compartment 165 which also fosters separation and capillarity. Capillarity is further enhanced due to the positioning and height differential between the inlet to the capillary channel 130 at the top of tower 144, and the relatively lower position of the test disk 160 that contains both the reaction capillary compartment 161 and the excess blood capillary compartment 165.

Figure 33:
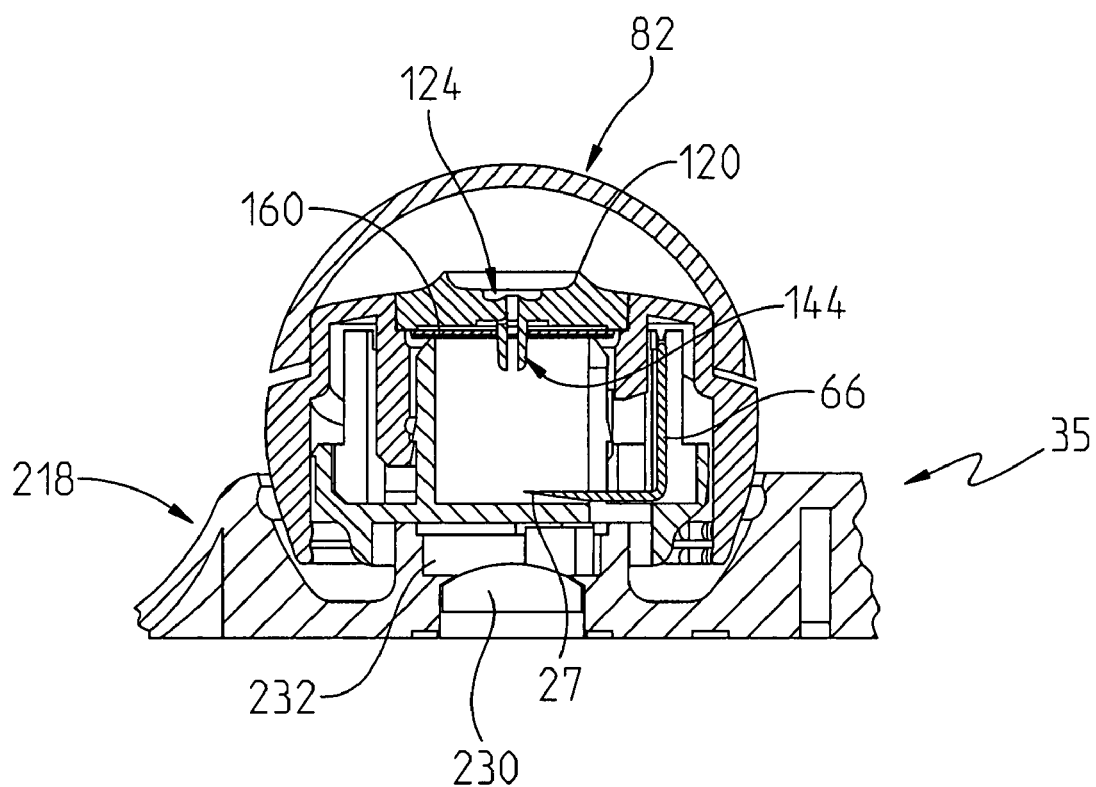
FIG. 33 is a sectional view showing the device mounted on to the meter of the present invention.

FIG. 33 presents another sectional view of the testing device 10, after the test is finished. After the testing is finished, the cap 82 is placed in its closed position, and the lens 230, can view the test results contained on the test member 160.

Figure 34:
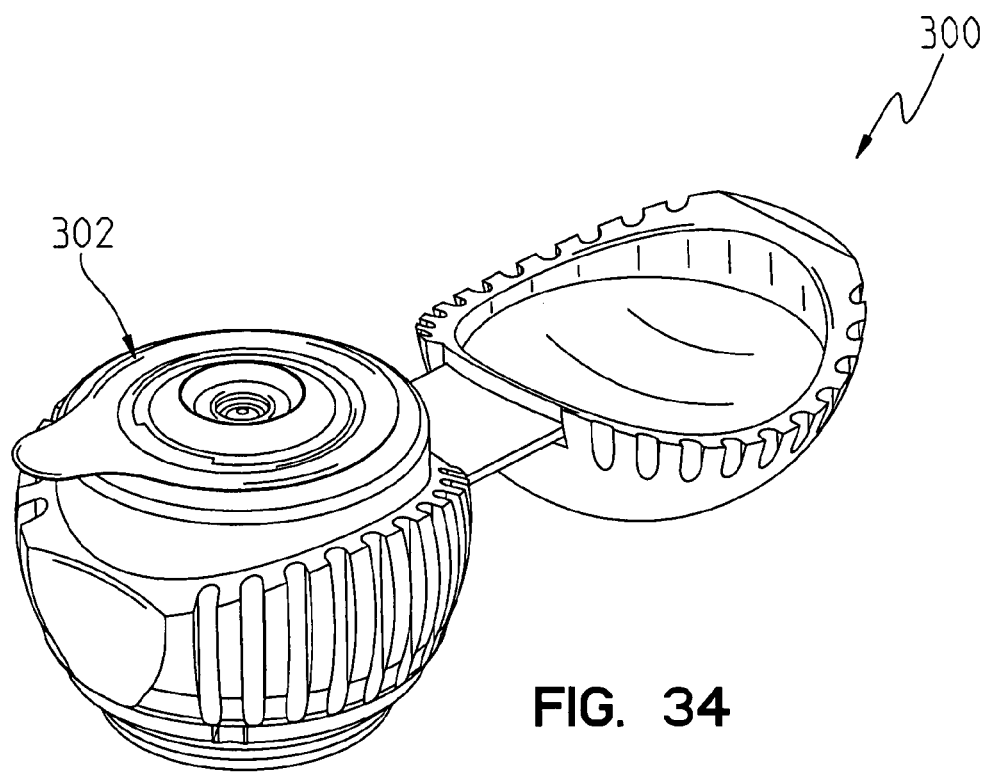
FIG. 34 is a perspective view of an alternate embodiment showing an alternate cleansing member.
Figure 35:
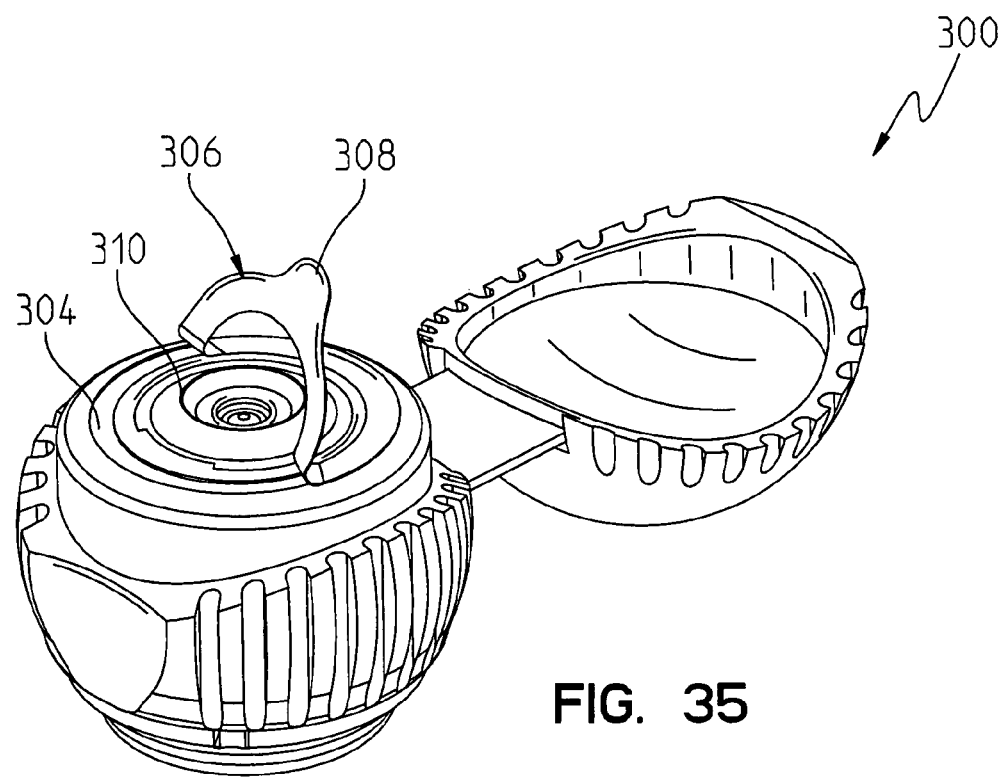
FIG. 35 is a perspective view of the embodiment of FIG. 34, showing the cover peel strip of the cleansing member partially removed.

FIGS. 34 and 35 disclose an alternate embodiment testing device 300. Testing device 300 is generally identical to testing device 10 shown in FIGS. 1-33, with the exception of the fact that testing device 300 includes a cleansing member 302 that is placed upon the body part supporting surface 20. The cleansing member 302 is generally ring-shaped, and includes a ring-shaped cleansing swab 304 that is disposed concentrically with and radially outwardly of the pressure cup 310. A cover member 306 covers the cleansing swab and includes a pull tab 308 to facilitate the user removing the cover member 306.

Cleansing swab 304 should preferably be fixedly coupled, such as by glue, to the testing device, or else, snugly fitted within a channel. Normally, it will be expected that cleansing swab will contain some sort of disinfectant, such as alcohol for which the user can cleanse his skin both prior to and after his body part is lanced.

Figure 36:
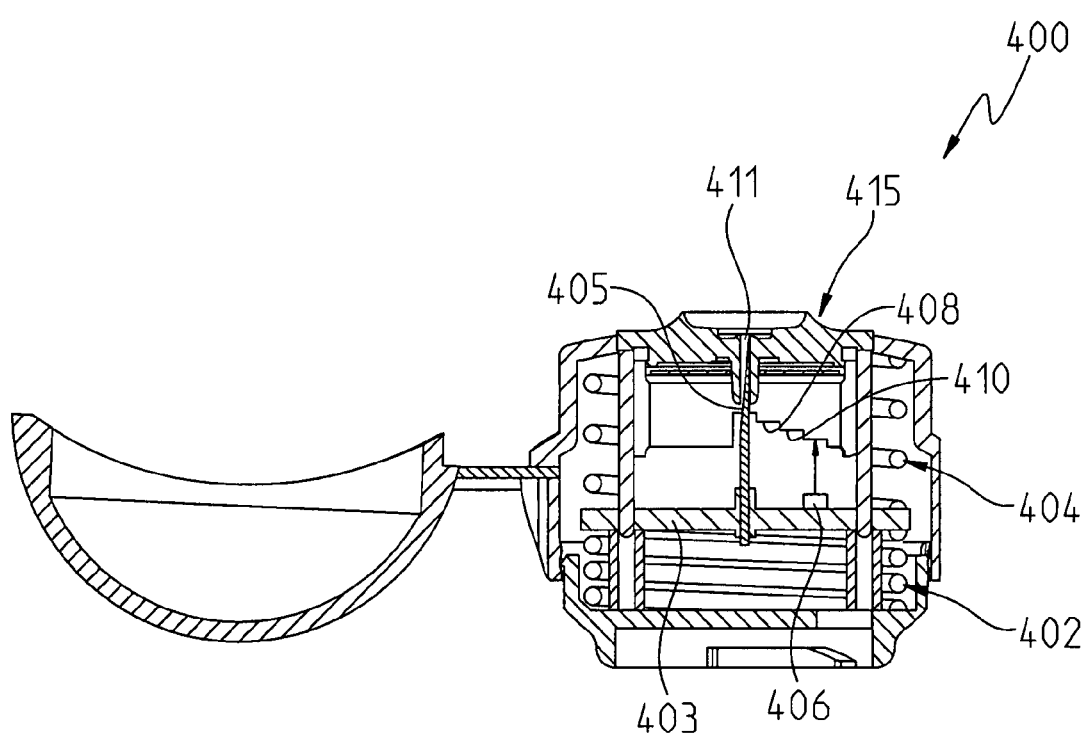
FIG. 36 is a sectional view of a second alternate embodiment, showing an alternate lance actuator.

FIG. 36 shows an alternate embodiment test device 400 wherein the lancet movement mechanism shown in FIGS. 1-35 is replaced by a spring-loaded lancet movement system. The lancet movement system includes a lancet moving spring 402 that is provided for engaging a platform 403 that supports lancet 405. This spring 402 expands to move platform 403 upwardly, to thereby move lancet 408 upwardly through the capillary channel 411, and into engagement with the user's body part. A lancet retraction spring 404 is provided for acting against the force exerted by the lancet moving spring 402 to cause the lancet 405 to retract downwardly, and back beneath the body part engaging surface 415, after the lancet pierces the skin of the user. A release member 406 is positioned to be engaged with one of several axially offset surfaces, e.g. 408, 410 that are designed and configured similarly to the axial offset surfaces discussed above in connection with FIGS. 1-33. The axially offset surfaces enable the user to adjust the depth to which the lancet 405 will penetrate their skin.

When the axially offset surface of choice (e.g. 408) contacts the release member 406, the spring 402 is then released to urge the lancet 405 upwardly and into engagement with the body part.

Although the invention has been described with reference to certain preferred embodiments, it will be appreciated that the scope and spirit of the above-referenced invention is not limited to the embodiments disclosed above, but is limited only by the broadest interpretation allowable of the claims as set forth below.

What is claimed:

1. A self contained disposable testing unit for testing body fluid comprising:
    a body member,
    a support member moveable with respect to the body member between a first position and a second position, the support member including a body part receiving surface for receiving a patient's body part,
    a lancet movable with respect to the support member, the lancet including a first end portion pivotably coupled to the body member for pivotal movement with respect to the body member, and a second end portion having a second end and a base end, the base end being disposed closer to the first end portion than the second end and the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip;
    a test member capable of interacting with body fluid to aid in determining information about body fluid components;
    a capillary member capable of directing fluid flow to the test member,
    a pressure cup for exerting pressure on a body part to foster fluid flow out of a lanced site and into the capillary; and
    a calibration member capable of containing information for facilitating calibration of the testing unit.

2. The testing unit of claim 1 wherein the lancet is pivotably moveable between
    (1) a storage position wherein the lancet tip is disposed below the body part receiving surface of the support member,
    (2) a piercing position wherein the lancet tip is disposed above the body part receiving surface of the support member, and
    (3) a retracted position wherein the lancet tip is disposed below the body part receiving surface of the support member,
    wherein the lancet is moved into the retracted position through an engagement of the support member with the lancet as the support member moves between the first and the second position.

3. The testing unit of claim 2 wherein the lancet moves generally perpendicularly to a patient's skin when the lancet pierces a patient's skin as the lancet moves between the storage position and the piercing position, and wherein the lancet assumes the piercing position when the support member is positioned between the first position and the second position.

4. The testing unit of claim 2 wherein the body member includes a lancet movement resisting surface for providing resistance to movement of the lancet into the retracted position.

5. The testing unit of claim 2 wherein the lancet includes a first end pivotably coupled to the body member to permit the lancet tip to move in an arcuate path between the piercing position and the retracted position.

6. The testing unit of claim 2 wherein the body member and the support member share a common axis and wherein the support and body members are rotatable relative to each other about the common axis for permitting the user to vary a distance into which the lancet can penetrate the skin when in the piercing position.

7. The testing unit of claim 6 wherein the support member includes at least a first and a second surface that are axially offset and selectively engagable with the lancet for moving the lancet to the retracted position, the first and second surfaces being circumferentially offset so that rotational movement of the support member causes a different one of the at least first and second surfaces to engage the lancet.

8. The testing unit of claim 2 wherein the support member includes at least a first and a second surface that are selectively engagable with the lancet for moving the lancet to the retracted position, wherein the first and second selectively engagable surfaces are axially offset, such that when the first surface engages the lancet, a depth to which the tip will penetrate a patient's skin is different than a depth to which the tip will penetrate a patient's skin when the second surface engages the lancet.

9. The testing unit of claim 2 further comprising a retraction spring for moving the lancet from the piercing position to the retracted position.

10. The testing unit of claim 2 wherein the lancet is pivotably movable between the piercing position and the retracted position.

11. The testing unit of claim 1 wherein at least one of the capillary member and test member include a reaction capillary compartment and an excess blood capillary compartment, and wherein blood components are separated by the test unit by a capillary force differential between the reaction capillary compartment and the excess blood capillary compartment.

12. The testing unit of claim 11 wherein the capillary force differential is caused by height difference between the reaction blood capillary compartment and the excess blood capillary compartment.

13. The testing unit of claim 12 wherein said height differential is generated by a bending of the reagent containing test member wherein bending is activated by at least one of a user pressing against the support member or bending is activated by a user releasing pressure against the support member.

14. The testing unit of claim 1 wherein the support member includes the capillary member, and the testing member comprises a reagent containing test member disposed downstream of the capillary member.

15. The testing unit of claim 1 further comprising a lancet position adjustor for permitting a user to vary a distance into which the lancet can penetrate a patient's skin when in the piercing position and a cap member hingedly coupled to the support member and moveable between a closed position where the cap member overlays and covers the support member, and an open position wherein the support member is uncovered and capable of receiving a body part.

16. The testing unit of claim 1 where the lancet includes a radially extending portion that extends radially between the first and second end portions so that the first and second end portions extend in a parallel, non-collinear relation.

17. The testing unit of claim 1 wherein the support member includes a capillary portion for separating body fluid components from whole body fluid in fluid communication with the body part receiving surface, and a reagent containing test member disposed downstream of the capillary portion.

18. The testing unit of claim 1 wherein the lancet can move into a piercing position wherein the lancet tip is disposed above the body part receiving surface further comprising a lancet position adjustor for permitting a user to vary a distance above the body part receiving surface that the lancet can extend.

19. The testing unit of claim 1 wherein the test member is capable of being read by a digital camera, and includes a mounting member for mounting the test member to a digital camera.

20. The testing unit of claim 1 wherein the calibration member is capable of being read by a digital camera.

21. The testing unit of claim 1 further comprising a cleansing member integrated into the testing unit.

22. The testing device of claim 1 wherein the first end portion extends generally chordally and the second end portion extends generally axially, whereby pivotal movement of the first end portion relative to the body member causes the tip of the second end portion to move in an arc generally perpendicular to the body receiving surface.

23. A self contained disposable testing unit for testing body fluid comprising:
 a body member
 a support member moveable with respect to the body member between a first position and a second position, the support member including a body part receiving surface for receiving a patient's body part,
 a lancet including a first end portion pivotably coupled to the body member for pivoting movement with respect to the body member, and a second end portion having a second end and a base end, the base end being disposed closer to the first end portion than the second end and a the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip;
 the lancet being pivotably moveable between
  (1) a storage position wherein the tip is disposed below the body part receiving surface of the support member,
  (2) a piercing position wherein the tip is disposed above the body part receiving surface of the support member, and
  (3) a retracted position wherein the tip is disposed below the body part receiving surface of the support member,
 wherein the lancet is moved into the retracted position through an engagement of the support member with the lancet as the support member moves between the first and the second position
 a test member capable of interacting with body fluid to aid in determining information about body fluid components;
 a capillary member capable of directing fluid flow to the test member,
 a pressure cup for exerting pressure on a body part to foster fluid flow out of a lanced site and into the capillary;
 a calibration member capable of containing information for facilitating calibration of the testing unit; and
 a lancet position adjustor for permitting a user to vary a distance into which the lancet can penetrate a patient's skin when in the piercing position, and wherein the lancet strikes a skin surface generally perpendicularly to the skin surface.

24. The testing unit of claim 23 wherein when the lancet is in the storage position, the lancet is carried by the body portion in a fixed position, and the support member includes at least a first and a second surface that are selectively engagable with the lancet for moving the lancet to the retracted position.

25. The testing unit of claim 24 wherein the first and second selectively engageable surfaces are axially offset, such that when the first surface engages the lancet, a depth to which the tip will penetrate a patient's skin is different than a depth to which the tip will penetrate a patient's skin when the second surface engages the lancet.

26. The testing unit of claim 24 wherein the lancet includes a radially extending portion extending between the first end portion and the second end portion, and the second end portion extends parallel with but not collinear with the first end portion.

27. The testing unit of claim 26 wherein the first end portion of the lancet is pivotably coupled to the body member, to permit the lancet to pivotally move in an arc between the piercing position and the retracted position.

28. The testing unit of claim 27 wherein the body member includes a lancet movement resisting surface for providing resistance to movement of the lancet into the retracted position without preventing the movement of the lancet into the retracted position.

29. The testing device of claim 26 wherein the radially extending portion extends generally perpendicularly to the first end portion, and the second end portion extends generally perpendicularly to the each of the first end portion and radially extending portion.

30. The testing unit of claim 26 wherein the radially extending portion extends generally perpendicularly to each of the first end portion and the second end portion, and the second end portion extends generally perpendicularly to each of the first end portion and radially extending portion.

31. A testing system for testing body fluid comprising a digital camera containing device having a case, and a self contained disposable testing unit for testing body fluid, the self-contained testing unit comprising:
 a body member,
 a support member moveable with respect to the body member between a first position and
 a second position, the support member including a body part receiving surface for receiving a patient's body part, a lancet carried by the body member and including a lancet tip capable of piercing a patient's skin to produce fluid flow;

a test member capable of interacting with body fluid to aid in determining information about body fluid components;

a capillary member capable of directing fluid flow to the test member, and a calibration member capable of containing information for facilitating calibration of the testing unit further comprising a coupler for coupling the testing unit to the case of the digital camera containing device capable of reading a test result on the reagent containing test member.

32. The testing unit of claim 31 wherein the body member includes a base that includes the coupler and an aperture for permitting a direct line of sight between the camera and the reagent containing test member, and wherein the coupler comprises at least one of a bayonet mount type coupler and a screw mount type coupler.

33. The testing device of claim 31 wherein the lancet includes a first end portion coupled to the body member, and a second end portion includes a piercing tip disposed generally perpendicularly to the first end portion.

34. The testing device of claim 31 wherein the lancet is pivotably coupled to the body member for pivoting movement with respect to the body member, wherein the support member is movable with respect to the lancet and engagable with the lancet to cause pivotal movement of the lancet.

35. A self contained disposable testing unit for testing body fluid comprising:

a body member a support member moveable with respect to the body member between a first position and a second position, the support member including a body part receiving surface for receiving a patient's body part, a lancet including a first end portion pivotably coupled to the body member for pivoting movement with respect to the body member, and a second end portion having a second end and a base end, the base end being disposed closer to the first end portion than the second end and the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip;

a test member capable of interacting with body fluid to aid in determining information about body fluid components;

a capillary member capable of directing fluid flow to the test member, pressure cup for exerting pressure on a body part to foster fluid flow out of a lanced site and into the capillary; and a calibration member capable of containing information for facilitating calibration of the testing unit wherein the support member is movable with respect to the lancet and engagable with the lancet to cause pivotal movement of the lancet tip in an arcuate path.

36. A self contained disposable testing unit for testing body fluid comprising:

a body member, a support member moveable with respect to the body member between a first position and a second position, the support member including a body part receiving surface for receiving a patient's body part, a lancet including a first end portion pivotably coupled to the body member for pivoting movement with respect to the body member, and a second end portion having a second end and a base end, the base end being disposed closer to the first end portion than the second end and the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip;

a test member capable of interacting with body fluid to aid in determining information about body fluid components;

a capillary member capable of directing fluid flow to the test member, a pressure cup for exerting pressure on a body part to foster fluid flow out of a lanced site and into the capillary; and a calibration member capable of containing information for facilitating calibration of the testing unit further comprising a skin distance member disposed interiorly of the pressure cup for maintaining a patient's body part at an appropriate position wherein a patient's body part will not engage an inlet to the capillary member.

37. A self contained disposable testing unit for testing body fluid comprising:

a body member, a support member moveable with respect to the body member between a first position and a second position, the support member including a body part receiving surface for receiving a patient's body part, a lancet including a first end portion pivotably coupled to the body member for pivoting movement with respect to the body member, and a second end portion having a second end and a base end, the base end being disposed closer to the first end portion than the second end and the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip;

a test member capable of interacting with body fluid to aid in determining information about body fluid components;

a capillary member capable of directing fluid flow to the test member, a pressure cup for exerting pressure on a body part to foster fluid flow out of a lanced site and into the capillary; and a calibration member capable of containing information for facilitating calibration of the testing unit wherein the support member is movable with respect to the lancet and engagable with the lancet to cause pivotal movement of the lancet toward the retracted position.

38. A self contained disposable testing unit for testing body fluid comprising:

a body member a support member moveable with respect to the body member between a first position and a second position, the support member including a body part receiving surface for receiving a patient's body part, a lancet including a first end portion pivotably coupled to the body member for pivoting movement with respect to the body member, and a second end portion having a second end and a base end, the base end being disposed closer to the first end portion than the second end and the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip; and wherein the lancet includes a radially extending portion extending between the first and the second end portions, wherein the support member is movable with respect to the lancet and engagable with the lancet to cause pivotal movement of the lancet a test member capable of interacting with body fluid to aid in determining information about body fluid components;

a capillary member capable of directing fluid flow to the test member, a pressure cup for exerting pressure on a body part to foster fluid flow out of a lanced site and into the capillary; and a calibration member capable of containing information for facilitating calibration of the testing unit.

39. A self contained disposable testing unit for testing body fluid comprising:

a body member a support member moveable with respect to the body member between a first position and a second position, the support member including a body part receiving surface for receiving a patient's body part, a lancet movable with respect to the support member, the lancet including a first end portion pivotably coupled to the body member for pivoting movement with respect to the body member, and a second end portion having a second end and a base end, the base end being disposed closer to the first end portion than the second end and the second end including a lancet tip capable of piercing a patient's skin to produce fluid flow, wherein during pivotal movement of the lancet, the base end and lancet tip of the second end portion move in an arcuate path and extend along a tangent of an arc scribed by the pivotal movement, wherein the base end follows the lancet tip;

a test member capable of interacting with body fluid to aid in determining information about body fluid components;

a capillary member capable of directing fluid flow to the test member.

40. The testing unit of claim 39 wherein the lancet includes a radially extending portion extending between the first end portion and the second end portion, and the second end portion extends parallel with but not collinear with the first end portion.

41. The testing device of claim 40 wherein the radially extending portion extends generally perpendicularly to the first end portion, and the second end portion extends generally perpendicularly to the each of the first end portion and radially extending portion.

* * * * *